US010800715B2

(12) United States Patent
Miyazawa et al.

(10) Patent No.: US 10,800,715 B2
(45) Date of Patent: Oct. 13, 2020

(54) POLYMER-SUPPORTED TRANSITION CATALYST

(71) Applicant: TOYO GOSEI CO., LTD., Chiba (JP)

(72) Inventors: Takashi Miyazawa, Chiba (JP); Shin-ya Tashita, Chiba (JP)

(73) Assignee: TOYO GOSEI CO., LTD., Chiba (JP)

( * ) Notice: Subject to any disclaimer, the term of this patent is extended or adjusted under 35 U.S.C. 154(b) by 25 days.

(21) Appl. No.: 16/408,874

(22) Filed: May 10, 2019

(65) Prior Publication Data

US 2019/0263728 A1   Aug. 29, 2019

Related U.S. Application Data

(63) Continuation of application No. 15/510,463, filed as application No. PCT/JP2015/075940 on Sep. 12, 2015, now Pat. No. 10,308,562.
(Continued)

(51) Int. Cl.
| | | |
|---|---|---|
| C07B 37/04 | (2006.01) | |
| B01J 21/04 | (2006.01) | |
| B01J 23/40 | (2006.01) | |
| B01J 35/06 | (2006.01) | |
| C07C 5/09 | (2006.01) | |
| C07C 67/293 | (2006.01) | |

(Continued)

(52) U.S. Cl.
CPC ............... *C07B 37/04* (2013.01); *B01J 21/04* (2013.01); *B01J 21/063* (2013.01); *B01J 21/066* (2013.01); *B01J 21/08* (2013.01); *B01J 23/40* (2013.01); *B01J 23/42* (2013.01); *B01J 23/44* (2013.01); *B01J 23/462* (2013.01); *B01J 23/464* (2013.01); *B01J 23/52* (2013.01); *B01J 23/755* (2013.01); *B01J 31/06* (2013.01); *B01J 31/069* (2013.01); *B01J 31/127* (2013.01); *B01J 35/065* (2013.01); *B01J 37/02* (2013.01); *B01J 37/035* (2013.01); *B01J 37/06* (2013.01); *B01J 37/16* (2013.01); *B01J 37/18* (2013.01); *C07B 41/06* (2013.01); *C07B 47/00* (2013.01); *C07B 61/00* (2013.01); *C07C 1/00* (2013.01); *C07C 1/321* (2013.01); *C07C 2/00* (2013.01); *C07C 2/861* (2013.01); *C07C 5/08* (2013.01); *C07C 5/09* (2013.01); *C07C 45/32* (2013.01); *C07C 45/34* (2013.01); *C07C 49/04* (2013.01); *C07C 51/353* (2013.01); *C07C 67/293* (2013.01); *C07C 67/303* (2013.01); *C07C 69/157* (2013.01); *C07C 69/612* (2013.01); *C07C 209/36* (2013.01); *C07F 7/1876* (2013.01); *C08K 3/04* (2013.01); *C08K 3/10* (2013.01); *C08K 3/22* (2013.01); *C08K 3/36* (2013.01); *B01J 2231/323* (2013.01); *B01J 2231/4211* (2013.01); *B01J 2231/4261* (2013.01); *B01J 2231/4266* (2013.01); *B01J 2231/641* (2013.01); *B01J 2231/645* (2013.01); *B01J 2231/70* (2013.01); *B01J 2531/18* (2013.01); *B01J 2531/821* (2013.01); *B01J 2531/822* (2013.01); *B01J 2531/824* (2013.01); *B01J 2531/828* (2013.01); *B01J 2531/847* (2013.01); *C07C 2521/04* (2013.01); *C07C 2521/06* (2013.01); *C07C 2521/08* (2013.01); *C07C 2521/10* (2013.01); *C07C 2521/18* (2013.01); *C07C 2523/42* (2013.01); *C07C 2523/44* (2013.01); *C07C 2523/46* (2013.01); *C07C 2523/52* (2013.01); *C07C 2523/755* (2013.01); *C07C 2531/06* (2013.01); *C08K 2003/222* (2013.01); *C08K 2003/2227* (2013.01); *C08K 2003/2241* (2013.01); *C08K 2003/2244* (2013.01)

(58) Field of Classification Search
None
See application file for complete search history.

(56) References Cited

U.S. PATENT DOCUMENTS

| | | | |
|---|---|---|---|
| 4,677,095 A | 6/1987 | Wan | |
| 5,561,231 A * | 10/1996 | Dauth | C07F 7/1876 546/2 |

(Continued)

FOREIGN PATENT DOCUMENTS

| | | |
|---|---|---|
| CN | 103127954 A | 6/2013 |
| JP | 2002-253972 A | 9/2002 |

(Continued)

OTHER PUBLICATIONS

Conley et al., ACS Catal. 2014, 4, 1458-1469) (Year: 2014).*
(Continued)

*Primary Examiner* — Clinton A Brooks
*Assistant Examiner* — Kofi Adzamli
(74) *Attorney, Agent, or Firm* — Maier & Maier, PLLC

(57) ABSTRACT

A long life catalyst is provided that is conveniently and inexpensively capable of being produced and that is highly active and has inhibited metal leakage. According to aspects of the present invention, a catalyst is provided that includes: a polymer including a plurality of first structural units and a plurality of second structural units; and metal acting as a catalytic center, wherein at least part of the metal is covered with the polymer, each of the plurality of first structural units has a first atom constituting a main chain of the polymer and a first substituent group bonded to the first atom, a second atom included in each of the plurality of second structural units is bonded to the first atom, and the second atom is different from the first atom, or at least one of all substituent groups on the second atom is different from the first substituent group.

7 Claims, 1 Drawing Sheet

Related U.S. Application Data

(60) Provisional application No. 62/050,044, filed on Sep. 12, 2014.

(51) Int. Cl.

| | | |
|---|---|---|
| C07C 67/303 | (2006.01) |
| C07C 69/157 | (2006.01) |
| C07C 69/612 | (2006.01) |
| C07B 61/00 | (2006.01) |
| C07C 209/36 | (2006.01) |
| C07C 1/00 | (2006.01) |
| C07C 45/32 | (2006.01) |
| C07C 2/00 | (2006.01) |
| C07C 49/04 | (2006.01) |
| C07C 51/353 | (2006.01) |
| B01J 31/06 | (2006.01) |
| B01J 31/12 | (2006.01) |
| B01J 21/06 | (2006.01) |
| B01J 21/08 | (2006.01) |
| B01J 37/02 | (2006.01) |
| B01J 23/42 | (2006.01) |
| B01J 23/44 | (2006.01) |
| B01J 23/46 | (2006.01) |
| B01J 23/52 | (2006.01) |
| B01J 23/755 | (2006.01) |
| B01J 37/03 | (2006.01) |
| B01J 37/06 | (2006.01) |
| B01J 37/16 | (2006.01) |
| B01J 37/18 | (2006.01) |
| C07B 41/06 | (2006.01) |
| C07B 47/00 | (2006.01) |
| C07C 1/32 | (2006.01) |
| C07C 2/86 | (2006.01) |
| C07C 5/08 | (2006.01) |
| C07C 45/34 | (2006.01) |
| C07F 7/18 | (2006.01) |
| C08K 3/04 | (2006.01) |
| C08K 3/10 | (2018.01) |
| C08K 3/22 | (2006.01) |
| C08K 3/36 | (2006.01) |

(56) References Cited

U.S. PATENT DOCUMENTS

| | | |
|---|---|---|
| 8,765,628 B2 | 7/2014 | Bai |
| 2004/0077905 A1 | 4/2004 | Kobayashi |
| 2008/0076662 A1 | 3/2008 | Kobayashi |
| 2015/0051357 A1 | 2/2015 | Komati et al. |

FOREIGN PATENT DOCUMENTS

| | | | |
|---|---|---|---|
| JP | 2013-031806 A | | 2/2013 |
| JP | 2013031806 A | * | 2/2013 |
| JP | 2014-091092 A | | 5/2014 |
| WO | 2012/111468 A1 | | 8/2012 |
| WO | 2013/158272 A1 | | 10/2013 |

OTHER PUBLICATIONS

Kobayashi—JP-2013031806-A—Machine Translation (Year: 2013).*
International Search Report dated Dec. 1, 2015 of corresponding application No. PCT/JP2015/075940; 6 pgs.
J. Am. Chem. Soc., 1971, 93, 3062-3063.; 1 pg.
Angew. Chem. Int. Ed. 2000, 39, 3896-3898.; 3 pgs.
Chinese Office Action dated Feb. 1, 2019, in connection with counterpart CN Application No. 201580048437.5 (14 pgs., including machine-generated English translation).
Chinese Office Action dated Oct. 24, 2019, in connection with corresponding CN Application No. 201580048437.5 (14 pgs., including machine-generated English translation).

* cited by examiner

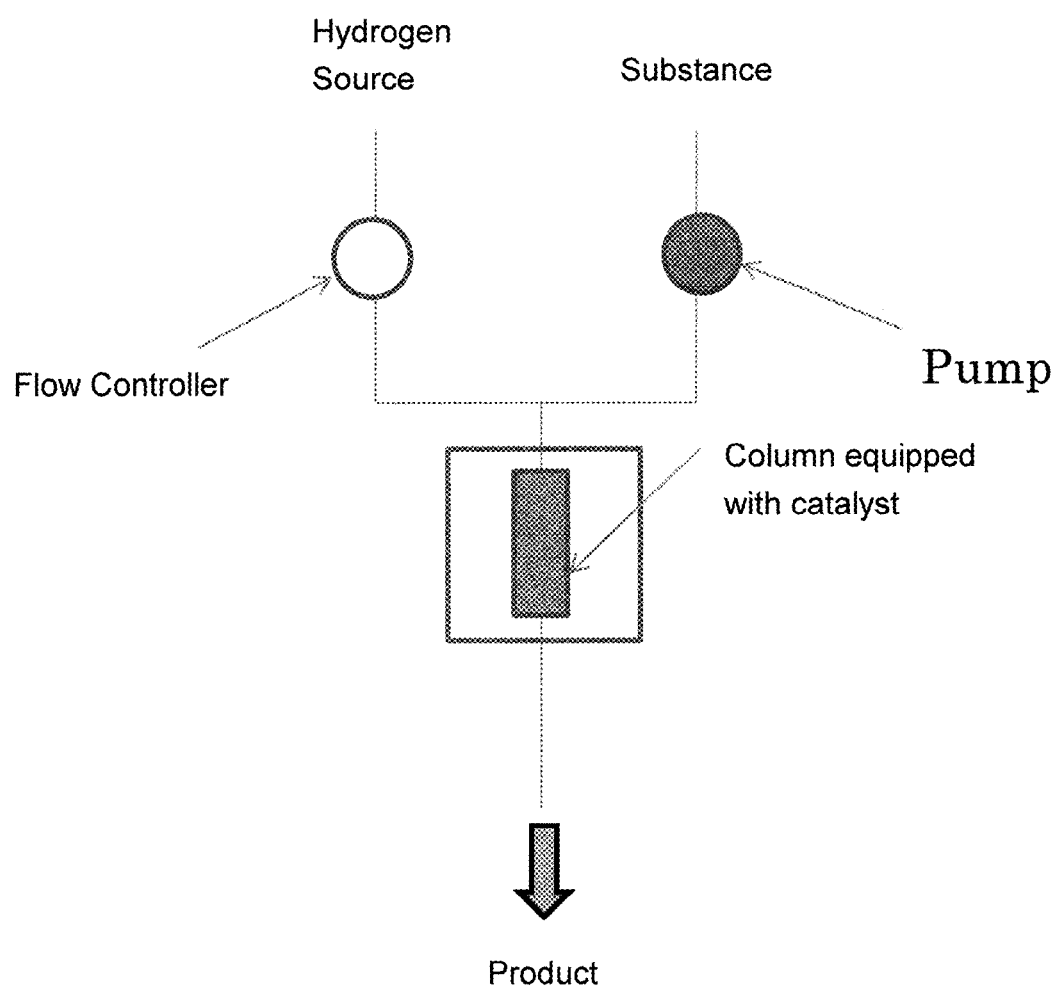

POLYMER-SUPPORTED TRANSITION CATALYST

TECHNICAL FIELD

Aspects of the present invention relate to a catalyst of a composition that is composed of a complex of metal supported by at least a polymer, the catalyst being highly active, readily produced and handled, and excellent in durability allowing repeated or continued use.

BACKGROUND ART

Metal is utilized as an important constituent of a catalyst for chemical reaction. Even in the case of being limited to the field of organic synthesis, catalysts including metal, particularly transition metal, are applied to various types of reactions, such as reduction reaction, oxidation reaction, hydrometalation, carbon-carbon bond forming reaction, and carbon-nitrogen bond forming reaction, and are reagents indispensable for production of a large amount of industrial products, pharmaceutical products, or agricultural chemicals.

Meanwhile, transition metal includes many rare elements, such as platinum and palladium, which are classified into rare metal and are often expensive because the reserves and the production volume are limited. Accordingly, from the perspective of costs and effective use of resources, there is a demand for recycling transition metal. For further efficiency, there is also a strong request for recovering and reusing a transition metal catalyst.

As a technique for recovering and reusing or continuously using a transition metal catalyst, a transition metal catalyst has been immobilized on a polymer or an inorganic material.

For example, a report describes that, reduction reaction that is hydrogenation of the carbon-carbon double bond proceeds using a catalyst having rhodium as transition metal supported by polystyrene having phosphine as a substituent group that can coordinate to rhodium (NPL 1).

In another example, olefin metathesis reaction proceeds using a catalyst including ruthenium supported by polyethylene glycol having carbene or phosphine as a substituent group that can coordinate to ruthenium, and a polyethylene glycol supported catalyst is recovered by adding diethyl ether as a poor solvent (NPL 2).

In the case of using palladium, allylation reaction is carried out by being supported by polystyrene to successfully recover the catalyst (PTL 1).

CITATION LIST

Patent Literature

PTL 1: JP 2002-253972A

Non Patent Literature

NPL 1: J. Am. Chem. Soc., 1971, 93, 3062-3063.
NPL 2: Angew. Chem. Int. Ed. 2000, 39, 3896-3898.

SUMMARY OF THE INVENTION

Technical Problem

However, as described above, when a substituent group that can coordinate to metal included in a catalyst is introduced to a polymer or an inorganic carrier to immobilize the catalyst on the polymer or the inorganic carrier, the step of introducing a coordination site to the polymer is required, and depending on combination of the coordination site with the polymer, there are sometimes problems, such as difficulty of synthesis and increase in costs.

Aspects of the present invention are carried out to solve the problems, and provide a long life catalyst that is capable of being conveniently and inexpensively produced and that is highly active or has inhibited metal leakage.

Solution to Problem

According to some aspects of the present invention, a catalyst is provided that includes: a polymer including a plurality of first structural units and a plurality of second structural units; and a metal acting as a catalytic center, wherein:
at least part of the metal is covered with the polymer;
each of the plurality of first structural units has a first atom constituting a main chain of the polymer and a first substituent group bonded to the first atom;
a second atom included in each of the plurality of second structural units is bonded to the first atom; and
the second atom is different from the first atom, or at least one of all substituent groups on the second atom is different from the first substituent group.

The inventors made a review to strongly immobilize a metal on a polymer and found that the metal is effectively immobilized using some polymers that are readily synthesized or available as a carrier. In addition, when a composition composed of a metal and the polymer including the metal is used as a catalyst, various organic synthesis chemical reactions smoothly proceeded to successfully produce a target compound in high yield. Moreover, they have made it clear that the catalyst does not cause metal leakage after reaction and is excellent in durability.

With regard to the catalyst, it is preferred that the main chain of the polymer does not include a carbon atom.

With regard to any one of the catalysts, it is preferred that each of the first atom and the second atom is not a carbon atom.

With regard to any one of the catalysts, it is preferred that the first atom is a silicon atom.

With regard to any one of the catalysts, it is preferred that the second atom may be an oxygen atom or a nitrogen atom.

With regard to any one of the catalysts, it is preferred that the metal may be any one selected from the group consisting of palladium, platinum, ruthenium, rhodium, silver, gold, copper, nickel, cobalt, iron, chromium, manganese, technetium, osmium, molybdenum, tungsten, iridium, rhenium, titanium, zirconium, hafnium, tantalum, niobium, and vanadium.

With regard to any one of the catalysts, it is preferred that the first atom is a silicon atom, and the first substituent group is preferably at least any one selected from the group consisting of a substituent group constituted only of a hydrogen atom, a substituent group including an oxygen atom, and a substituent group including a carbon atom.

With regard to any one of the catalysts, it is preferred that the catalyst further includes an inorganic member or an organic member.

With regard to any one of the catalysts, it is preferred that the catalyst further includes an alumina or a silicon oxide.

A method of producing a catalyst of some aspects according to the present invention includes:

a first step of preparing a first compound containing a metal atom and a polymer containing a plurality of first structural units and a plurality of second structural units; and a second step of reacting the first compound and the polymer, wherein:

at least one first structural unit of the plurality of first structural units has a first atom constituting a main chain of the polymer and a first substituent group bonded to the first atom;

a second atom included in each of the plurality of second structural units is bonded to the first atom, the second atom is different from the first atom, or at least one of all substituent groups on the second atom is different from the first substituent group; and in the second step, the first substituent group reacts with the first compound.

With regard to any one of the methods, it is preferred that the first atom is a silicon atom, and the first substituent group is preferably a hydrogen atom.

With regard to any one of the methods, it is preferred that the second atom has an electronegativity higher than an electronegativity of the first atom.

With regard to any one of the methods, it is preferred that in the second step, the metal atom is inserted between the silicon atom and the hydrogen atom.

A method of producing a compound according to the present invention includes any one selected from the group consisting of reduction reaction, oxidation reaction, hydrometalation, carbon-carbon bond forming reaction, and carbon-nitrogen bond forming reaction using the catalyst of any one of the above to form the compound.

That is, according to the above aspects of the present invention, a highly durable catalyst having metal strongly immobilized on a polymer is provided. A method of producing the catalyst and a method of producing a compound using the catalyst are also provided.

A method of producing a composition according to other aspects of the present invention includes the steps of: preparing a first compound containing a first atom of group 14 and a second atom and a second compound containing a third atom as metal; and a first reaction to react the first compound with the second compound. In the first reaction, the third atom is preferably oxidized or reduced.

With regard to the method, it is preferred that the first reaction is performed in a first solvent.

With regard to the method, it is preferred that the first compound further contains a fourth atom.

With regard to the method, it is preferred that the first compound has a first bond between the first atom and the second atom.

With regard to the method, it is preferred that the first compound has a second bond between the first atom and the fourth atom.

With regard to the method, it is preferred that each of the second atom and the fourth atom is a hydrogen atom.

With regard to the method, it is preferred that the method further includes the step of preparing a third compound having a third bond between a hydrogen atom and a fifth atom having an electronegativity higher than an electronegativity of the hydrogen atom. It is preferred that the first reaction is performed in the presence of the third compound.

With regard to the method, it is preferred that a bond between the first atom and the fifth atom is formed during the first reaction. Typical examples of the bond are an oxygen-silicon bond and a nitrogen-silicon bond.

With regard to the method, it is preferred that the fifth atom is one of an oxygen atom and a nitrogen atom.

With regard to the method, it is preferred that the first compound has a fourth bond between the first atom and the oxygen atom.

With regard to the method, it is preferred that the first compound further contains a sixth atom and the sixth atom is of group 14.

With regard to the method, it is preferred that the first atom and the sixth atom are bonded to an identical oxygen atom.

With regard to the method, it is preferred that both the first atom and the sixth atom are silicon atoms.

With regard to the method, it is preferred that the first compound further contains a plurality of seventh atoms, the plurality of seventh atoms are of group 14, and two of the plurality of seventh atoms which are closest mutually among the plurality of seventh atoms are bonded to an eighth atom.

With regard to the method, it is preferred that the eighth atom is an oxygen atom.

With regard to the method, it is preferred that the first compound has a siloxane moiety.

With regard to the method, it is preferred that the first compound is a polysiloxane.

With regard to the method, it is preferred that a hydrogen molecule is generated during the first reaction.

With regard to the method, it is preferred that the hydrogen molecule reduces the third atom.

With regard to the method, it is preferred that the first compound has the average molecular weight greater than 500.

With regard to the method, it is preferred that the first compound has the average molecular weight greater than of 1000.

With regard to the method, it is preferred that the further includes the step of adding a first raw material to the first solvent after the first reaction.

With regard to the method, it is preferred that a first member is capable of supporting the third atom.

With regard to the method, it is preferred that the third atom is supported by the first member after the third atom is oxidized or reduced.

With regard to the method, it is preferred that the first member has at least each one of a silicon-oxygen bond and an aluminum-oxygen bond.

With regard to the method, it is preferred that the first member is an alumina or a silicon oxide.

With regard to the method, it is preferred that the method further includes the step of agglutinating of particles each of which contains the third atom.

With regard to the method, it is preferred that the agglutinating of the particles is performed by an addition of a second solvent.

With regard to the method, it is preferred that the agglutinating of the particles preferably occurs after oxidization or reduction of the third atom.

With regard to the method, it is preferred that the method further includes the step of adding a first member to the first solvent after the first reaction.

With regard to the method, it is preferred that the agglutinating of the particles is performed after the adding of the first member.

With regard to the method, it is preferred that the third compound further includes a fifth bond between a ninth atom and a tenth atom.

With regard to the method, it is preferred that an element of the fifth atom is identical with an element of the ninth atom, and the tenth atom is a hydrogen atom.

With regard to the method, it is preferred that the method further includes the step of reprecipitating to collect the particles. Each of the particles supports the third atom which has been oxidized or reduced.

With regard to the method, it is preferred that the third atom is a transition metal atom.

With regard to the method, it is preferred that the third atom is any one selected from the group consisting of palladium, ruthenium, platinum, and rhodium.

With regard to the method, it is preferred that the composition is capable of acting as a catalyst for organic synthesis reaction.

With regard to the method, it is preferred that the organic synthesis reaction is any one selected from the group consisting of hydrogenation reaction, carbon-carbon bond forming reaction, and hydrosilylation reaction.

With regard to the method, it is preferred that the ratio of the third atom to the first atom by weight in the composition is equal to or greater than 0.005.

With regard to the method, it is preferred that the ratio of the third atom to the first atom by weight in the composition is equal to or greater than 0.01.

With regard to the method, it is preferred that the ratio of the third atom to the first atom by weight in the composition is equal to or greater 0.05.

With regard to the method, it is preferred that the ratio of the third atom to the first atom by weight in the composition is equal to or greater than 0.01.

With regard to the method, it is preferred that the method further includes removing at least one of the first compound and a fifth compound generated by a second reaction involved with the first compound.

A composition according to some aspects of the present invention includes: a first atom of group 14; a second atom; and a third atom as a metal. It is preferred that the ratio of the third atom to the first atom by weight in the composition is equal to or greater than 0.005.

With regard to the composition, it is preferred that the ratio of the third atom to the first atom by weight in the composition is equal to or greater than 0.01.

With regard to the composition, it is preferred that the ratio of the third atom to the first atom by weight in the composition is equal to or greater than 0.05.

With regard to the composition, it is preferred that the ratio of the third atom to the first atom by weight in the composition is equal to or greater than 0.01.

With regard to the composition, it is preferred that the first atom is any one selected from the group consisting of a silicon atom, a germanium atom, a tin atom, and a lead atom.

With regard to the composition, it is preferred that the third atom is a transition metal atom.

With regard to the composition, it is preferred that the third atom is any one selected from the group consisting of palladium, ruthenium, platinum, and rhodium.

With regard to the composition, it is preferred that the second atom is any one selected from the group consisting of a nitrogen atom and an oxygen atom.

With regard to the composition, it is preferred that the first atom bonds to the second atom.

With regard to the composition, it is preferred that the composition is capable of acting as a catalyst in organic synthesis reaction.

With regard to the composition, it is preferred that the composition further includes a fifth atom.

With regard to the composition, it is preferred that the ratio of the first atom to the fifth atom by weight is equal to or smaller than 1.0.

With regard to the composition, it is preferred that the composition further includes a sixth atom. It is preferred that the fifth atom is bonded to the sixth atom.

With regard to the composition, it is preferred that an element of the second atom is preferably identical with an element of the sixth atom.

With regard to the composition, it is preferred that the second atom is an oxygen atom.

With regard to the composition, it is preferred that the first atom is not bonded to an atom of group 14.

With regard to the composition, it is preferred that the first atom is a silicon atom.

A composition according to some aspects of the present invention includes: a plurality of first atoms of a first element; a plurality of second atoms of a second element other than the first element; and a plurality of third atoms of a third element.

With regard to the composition, it is preferred that the plurality of first atoms is not bonded to each other; and each of the plurality of first atoms is bonded to one of the second atoms.

With regard to the composition, it is preferred that the ratio of the third element to the second element by weight in the composition is equal to or greater than 0.01.

With regard to the composition, it is preferred that the ratio of the third element to the second element by weight in the composition is equal to or greater than 0.05.

With regard to the composition, it is preferred that the ratio of the third element to the second element by weight in the composition is equal to or greater than 0.01.

With regard to the composition, it is preferred that the composition is not ignitable in air.

With regard to the composition, it is preferred that the composition further includes a plurality of fourth atoms of a fourth element other than the first element, the second element, and the third element.

With regard to the composition, it is preferred that the composition further includes a plurality of fifth atoms of a fifth element other than the first element and the third element.

With regard to the composition, it is preferred that each of the plurality of fourth atoms bonds to any one of the plurality of fifth atoms.

With regard to the composition, it is preferred that each of the second element and the fifth element is oxygen.

With regard to the composition, it is preferred that the ratio of the first element to the fourth element by weight is equal to or smaller than 1.0.

With regard to the composition, it is preferred that the ratio of the first element to the fourth element by weight is equal to or smaller than 0.5.

With regard to the composition, it is preferred that the ratio of the first element to the fourth element by weight is equal to or smaller than 0.1.

With regard to the composition, it is preferred that the first element is any one selected from the group consisting of silicon, germanium, tin, and lead.

With regard to the composition, it is preferred that the fourth element is aluminum.

With regard to the composition, it is preferred that the third element is any one of transition metals.

A method of producing a material according to some aspects of the present invention includes the steps of:

preparing any one of the compositions and a first substance; and reacting the first substance in the presence of the composition.

With regard to the method, it is preferred that the reaction is any one selected from the group consisting of reduction reaction, oxidation reaction, carbon-carbon bond forming reaction, and hydrosilylation reaction.

With regard to the method, it is preferred that the reaction is performed under flowing the first substance.

With regard to the method, it is preferred that the reaction is performed by flowing the first substance through the composition fixed to a flow path.

An equipment according to some aspects of the present invention includes: a flow path; and any one of the above compositions.

With regard to the equipment, it is preferred that the composition is configured such that a substance flowing through the flow path contacts the composition.

With regard to the equipment, it is preferred that the flow path is constituted by a column.

A method of producing a composition according to some aspects of the present invention includes the steps of: preparing a first compound containing a plurality of first atoms of group 14 and a plurality of second atoms and a second compound containing a third atom of a metal; and performing a first reaction of the first compound and the second compound.

With regard to the method, it is preferred that each of the plurality of first atoms is bonded to one of the plurality of second atoms; and the third atom is oxidized or reduced during the first reaction.

With regard to the method, it is preferred that the plurality of second atoms is hydrogen atoms.

With regard to the method, it is preferred that the plurality of first atoms is silicon atoms.

With regard to the method, it is preferred that the first compound has a fourth atom and two of the first atoms bonded to the fourth atom.

With regard to the method, it is preferred that the fourth atom is an oxygen atom.

With regard to the method, it is preferred that the method further includes steps of: preparing a third compound containing a hydrogen atom, and a fifth atom which has an electronegativity greater than an electronegativity of the hydrogen atom.

With regard to the method, it is preferred that the first reaction is performed in the presence of the third compound.

With regard to the method, it is preferred that the fifth atom is any one of a nitrogen atom and an oxygen atom.

With regard to the method, it is preferred that a bond between any one of the plurality of first atoms and the fifth atom is formed during the first reaction. Typical examples of the bond are an oxygen-silicon bond and a nitrogen-silicon bond.

With regard to the method, it is preferred that a hydrogen molecule is generated during the first reaction.

With regard to the method, it is preferred that the hydrogen molecule reduces the third atom.

BRIEF DESCRIPTION OF THE DRAWINGS

FIG. 1 is a conceptual diagram of an equipment in a flow reaction system.

DESCRIPTION OF EMBODIMENTS

The following describes some embodiments of the present invention. Various characteristics described in the following embodiments may be combined with each other. Each characteristic establishes an independent invention.

1. Polymer-Supported Metal Catalyst

A polymer-supported metal catalyst according to some aspects of the present invention is composed of a metal acting as a catalytic center and a polymer supported by the metal. Preferably, the polymer supporting the metal is further supported by an organic member or an inorganic member.

<Polymer>

The polymer may be any polymer without particular limitation to the type as long as the polymer is excellent in supporting ability to strongly immobilize metal as a catalytic center and is stable in the reaction conditions.

The polymer may be a homopolymer configured with repeated identical structural units, or may be a copolymer having a plurality of structural units that are equal to or more than two and different. The copolymer includes a random copolymer having randomly bonded different structural units and a block copolymer having repeated same structural units. Preferably, the polymer includes a plurality of first structural units and a plurality of second structural units, wherein each of the plurality of first structural units has a first atom constituting a main chain of the polymer and a first substituent group bonded to the first atom, a second atom included in each of the plurality of second structural units is bonded to the first atom, and the second atom is different from the first atom, or at least one of all substituent groups on the second atom is different from the first substituent group.

More preferably, each atomic group in the structural units and a substituent group on a second atomic group satisfy any one of the following requisites (1) to (7). Even more preferably, they simultaneously satisfy another requisite. Most preferably, they satisfy all the requisites.

(1) The main chain of the polymer does not include a carbon atom.
(2) The first atom is an atom other than an oxygen atom and a nitrogen atom.
(3) The first atom is a silicon atom.
(4) The second atom is an oxygen atom or a nitrogen atom.
(5) The first atom is a silicon atom, and the first substituent group is at least any one selected from the group consisting of a substituent group constituted only of a hydrogen atom, a substituent group including an oxygen atom, and a substituent group including a carbon atom.
(6) The first atom is a silicon atom, and the first substituent group is a hydrogen atom.
(7) The second atom has an electronegativity higher than an electronegativity of the first atom.

Representative examples of the polymer according to the present invention include: a polymer in which a 14th group element atom, such as a carbon atom and a silicon atom, and a 16th group element atom, such as an oxygen atom and a sulfur atom, are bonded; and a polymer in which a 14th element atom, such as a silicon atom, and a 15th group element atom, such as a nitrogen atom and a phosphorus atom, are bonded. The polymer may be a polymer, such as carbosilane, in which different 14th group element atoms are linked, or may be a polymer in which a π-electron system is linked via a linking group, such as a methylene group. An even more preferred polymer preferably has an organic group, such as an alkyl group and an alkoxy group, or a hydrogen atom on group 14 element atom. Specific examples of the polymer include: a polymer having a main chain composed of a carbon atom and a heteroatom, such as polyethyleneimine, polyester, and polymethylene phenylene isocyanate; polysiloxanes, such as poly(oxymethylhydrosilylene), poly(oxydimethylsilylene) (oxymethylhydrosilylene), poly(oxydimethylsilylene) (oxydihydrosilylene), poly(oxydimethylsilylene) (oxydiphenylsilylene), and poly(oxymethylphenylsilylene); polysilazanes, such as perhydropolysilazane, polydimethylsilazane, poly(dimethylmethyl)silazane, polymethylsilazane, poly(1,1-dimethyl-2-methylpolysilazane), poly(1,1-diphenyl-2-methylpolysilazane), poly(1,1-diphenyl-2-phenylpolysilazane), poly(1-methyl-1-phenyl-2-methylpolysilazane), and poly(poly(1-methyl-1-phenyl-2-phenylpolysilazane); and polysilanes, such as poly(methylene) (methylsilylene) and poly(methylene) (dimethylsilylene). The polymer may be synthesized in advance or may be generated in the reaction system during catalyst production. A preferably used polymer particularly includes a silicon atom and preferably has at least one hydrogen atom on the silicon atom. A silicon-hydrogen bond is capable of interacting with a transition metal, such as palladium ion, ruthenium ion, rhodium ion, and platinum ion, to reduce metal ions. Depending on the metal, the reduction sometimes generates a metal cluster exhibiting catalytic activity.

As an example, a polysiloxane analog is described in detail. The polymer has a main chain composed of a silicon atom and an oxygen atom. Further in detail, the main chain may be composed of repeated units derived from a single monomer having the same substituent group on silicon or may be composed of repeated units derived from equal to or more than two monomers having different substituent groups on silicon. In the latter case, the polymer may be particularly either a random copolymer or a block copolymer.

The polysiloxane analog preferably has a hydrogen atom at a certain ratio as a substituent group on silicon. The ratio of the hydrogen atom to all substituent groups on the silicon atoms is preferably determined in accordance with reduction efficiency required to reduce a target metal atom. When a hydrogen atom is included as a substituent group on the silicon atoms, the polysiloxane analog may also act as a reducing agent. In addition, when a hydrogen atom is included as a substituent group on the silicon atoms, the polysiloxane analog may reduce the target metal atom and change to a silanol group by a trace amount of moisture and the like. The silanol group is further subjected to a dehydration condensation, and then capable of forming a cross-linked structure. The silanol group is thus considered to immobilize and coat the target metal atom more effectively.

Typically, the polysiloxane analog preferably has the average molecular weight of equal to or more than 500. The average molecular weight is even more preferably equal to or more than 1000. The hydrogen content is preferably equal to or more than 60 g/mol. A too-high hydrogen content sometimes causes hydrogen gas generation when the polysiloxane analog reacts with the metal atom. The hydrogen content is thus preferably equal to or less than 200 g/mol.

The polysiloxane analog, such as poly(oxymethylhydrosilylene), poly(oxydimethylsilylene) (oxymethylhydrosilylene), and poly(oxydimethylsilylene) (oxydihydrosilylene), are readily synthesized or inexpensively available. The polysiloxane analog are also very stable and readily handled. Accordingly, mass production of a catalyst using the polysiloxane analog as a carrier for the metal is excellent in that the raw materials are readily available and no special facilities in consideration of deterioration of the raw materials and the like are required.

<Metal>

The metal acting as a catalytic center may be any metal compound as long as being applicable to the target reaction. The metal is preferably a transition metal compound including a transition metal element of the 3rd group to the 13th group. The metal more preferably includes palladium, platinum, ruthenium, rhodium, silver, gold, copper, nickel, cobalt, iron, chromium, manganese, technetium, osmium, molybdenum, tungsten, iridium, rhenium, titanium, zirconium, hafnium, tantalum, niobium, vanadium, and any other transition metal element.

Although the type of ligands of the transition metal and the valence of the transition metal are not particularly limited, palladium, platinum, gold, and any other transition metals are considered to be supported by a polymer as a 0-valent metal cluster when, for example, the step of using a reducing agent is included in the production of a catalyst.

In some aspects of the present invention, a transition metal compound that may be used for the production of a catalyst is considered not to have a ligand or to have an anionic ligand or a neutral ligand. Such anion may be halide ion, such as chloro-, bromo-, and iodo-ions, acetate, triflate, mesylate, alkoxide, acetylacetonate, trifluoroacetate, propionate, cyano, hexafluoroacetylacetonate, hydroxide ions, nitrate, sulfonate, and composite salts and hydrate thereof.

More specific examples include bis(2,4-pentanedionate) titanium (IV) oxide, dichlorotitanium diisopropoxide, tetra-n-butylorthotitanate, tetraethylorthotitanate, tetraisopropylorthotitanate, titanium (III) chloride, titanium (IV) chloride, bis(2,4-pentanedionate) vanadium (IV) oxide, vanadium (III) chloride, vanadium (IV) chloride, chromium (III) acetate, chromium (II) chloride, chromium (III) chloride, chromium (III) nitrate, pyridinium chlorochromate, pyridinium dichromate, tris(2,4-pentanedionate) chromium (III), manganese (II) acetate, manganese (III) acetate, manganese (II) chloride, manganese (II) nitrate, manganese (II), bis(hexafluoroacetylacetonato) manganese (II), bis(2,4-pentanedionate) manganese (II), tris(2,4-pentanedionate) manganese (III), iron (II) acetate, iron (III) oxalate, iron (II) chloride, iron (III) chloride, iron (III) nitrate, iron (II) sulfate, iron (III) sulfate, ferrocene (II), n-butylferrocene (II), tris(2,4-pentanedionate) iron (III), cobalt (II) acetate, bis(2,4-pentanedionate) cobalt (II), tris(2,4-pentanedionate) cobalt (III), cobalt (II) chloride, cobalt (II) nitrate, nickel (II) acetate, bis(2,4-pentanedionate) nickel (II), nickel (II) chloride, nickel (II) nitrate, nickel (II) oxalate, tetrakis(triphenylphosphine) nickel (0), potassium tetracyanonickelate (II), copper (I) acetate, copper (II) acetate, copper (I) bromide, copper (II) bromide, copper (I) chloride, copper (II) chloride, copper (I) iodide, copper (II) iodide, copper (II) nitrate, copper (II) sulfate, bis(2,4-pentanedionate) copper (II), potassium tetrachlorocupurate (II), zinc (II) acetate, bis(2,4-pentadionate) zinc (II), zinc (II) nitrate, zinc (II) sulfate, tetrakis(2,4-pentanedionate) zirconium (IV), zirconocene dichloride (IV), zirconium (IV) chloride, zirconium (IV) ethoxide, zirconium (IV) propoxide, zirconium (IV) nitrate, niobium (V) chloride, niobium (V) ethoxide, molybdenum (II) acetate, molybdenum (III) chloride, molybdenum (IV) chloride, molybdenum (V) chloride, bis(2,4-pentanedionate) molybdenum (IV) dioxide, ruthenium (III) chloride, rhodium (II) acetate, rhodium (III) chloride, rhodium (III) nitrate, bis(1,5-cyclooctadiene)-μ,μ'-dichlororhodium, tris(triphenylphosphine) rhodium (I) chloride, palladium (II) acetate, palladium (II) chloride, palladium (II) nitrate, bis(2,4-pentanedionate) palladium (II), tetrakis(triphenylphosphine) palladium (0), potassium tetrachloropalladate (II), silver (I) acetate, silver (I) trifluoromethanesulfonate, silver (I) chloride, silver (I) nitrate, silver (I) sulfate, silver (I) p-toluenesulfonate, cadmium (II) acetate, cadmium (II) chloride, cadmium (II) nitrate, cadmium (II) sulfate, acetylacetonato hafnium (IV), hafnium (IV) chloride, hafnium (IV) ethoxide, hafnium (IV) isopropoxide, hafnocene dichloride, hafnium (IV) trifluoromethanesulfonate, tantalum (V) chloride, tantalum (V) ethoxide, tungsten (IV) chloride, tungsten (IV) ethoxide, hexacarbonyl tungsten, tungstic acid, rhenium (III) chloride, rhenium (IV) chloride, rhenium (V) chloride, rhenium pentacarbonyl chloride, osmium (III) chloride, iridium (III) chloride, iridium (IV) chloride, platinum (II) chloride, platinum (IV) chloride, potassium hexachloroplatinate (IV), hexahydrate hexachloroplatinate (IV), tetrakis(triphenylphosphine) platinum (0), potassium tetrachloroplatinate (II), gold (I) chloride, gold (III) chloride, gold (III) bromide, potassium tetracyanoaurate (III), tetrachloroauric (III) acid, tetrachloroaurate (III) tetrahydrate, (triphenylphosphine) gold (I) chloride, mercury (I) acetate, mercury (II) acetate, mercury (I) chloride, mercury (II) chloride, mercury (I) nitrate, mercury (II) nitrate, mercury (I) sulfate, and mercury (II) sulfate.

<Inorganic Member, Organic Member>

The polymer-supported metal catalyst according to some aspects of the present invention may further include, in addition to a metal acting as a catalytic center and the polymer to support the metal, an inorganic member to support the polymer with the metal catalyst immobilized thereon or an organic member, such as a polystyrene resin and a polyacrylic resin.

As the inorganic member, a metal compound, activated carbon, and the like may be used. As metal oxide, a compound, such as silicon oxide ($SiO_2$) and oxide including, titanium, zirconium, magnesium, and aluminum, and any other metals, may be used. More specific examples include titanium oxide ($TiO_2$), zirconium oxide ($ZrO_2$), magnesium oxide (MgO), alumina ($Al_2O_3$), zeolite, and hydrotalcite.

2. Method of Producing Metal Catalyst Supported by Polymer

A method of producing a metal catalyst supported by a polymer includes the step of mixing the metal atom compound and the polymer for support of the metal on the polymer. The method may further include the step of mixing the compound and the polymer with an inorganic member or an organic member for further support of the polymer including the transition metal on the inorganic member or the organic member.

<Mixing>

In the step of mixing the metal compound with the polymer for support, a considered method is that the metal compound and the polymer compound are directly kneaded or are mixed together with a solvent. When the metal compound is reacted with a reducing agent to reduce the valence of the metal to be supported by the polymer, the method using a solvent for mixed is preferred.

<Solvent>

The type of solvent may be freely selected as long as it can dissolve or disperse the reactant to some extent. An organic solvent is preferably used that is capable of effectively mixing the polymer. To use a reducing agent, an aprotic organic solvent is preferred considering the reactivity. The aprotic organic solvent includes ether solvent, such as diethyl ether and tetrahydrofuran (THF), aromatic hydrocarbons, such as benzene and toluene, and halide hydrocarbons, such as dichloromethane and chloroform, and the like. Tetrahydrofuran (THF), toluene, and the like are preferably used.

<Reducing Agent>

To reduce a metal compound in the step of producing a catalyst, the type of reducing agent to be used may be selected appropriately. Examples of the reducing agent include metallic hydrogen complex compounds and metal hydrides, such as lithium aluminum hydride, diisobutylaluminum hydride, sodium borohydride, triphenyltin hydride, and tri-n-butyltin hydride, hydrosilanes, such as trichlorosilane, trimethylsilane, triethylsilane, trimethoxysilane, and triethoxysilane, borane derivatives, such as diborane, amine borane complex, and alkylborane, alcohols, such as methanol, ethanol, and isopropyl alcohol, formic acid, hydrogen gas, and any other reducing agents. In particular, sodium borohydride, triethylsilane, and hydrogen gas are preferred considering costs, safety, influence on the environment, and the like. When poly(oxydimethylsilylene)(oxymethylhydrosilylene) (PMHS) is used as the polymer, the polymer itself as a carrier acts as a reducing agent. Accordingly, a separate reducing agent does not have to be added, and the catalyst is prepared by a more convenient method.

<Conditions for Mixing and Reduction>

To mix the metal compound and the polymer in a solvent, a reaction temperature may be set any temperature that is equal to or less than the boiling point and equal to or more than the freezing point. However, when the metal compound has to be reduced, the reaction temperature is in a range to allow reduction reaction for the metal compound to proceed with no problems. At this point, a reducing agent is separately added if necessary, and if a polymer is prepared in the system, instead of the polymer, equal to or more than one type of corresponding monomer is appropriately added. In some aspects of the present invention, reduction reaction to a transition metal compound does not require a high temperature, and such reduction reaction is preferably carried out in a temperature range approximately from 0° C. to room temperature from the perspective of costs for facilities and utilities.

Further, to have the polymer supported by an inorganic member or an organic member, the inorganic member or the organic member is added to the reaction solution including a transition metal compound, a polymer, and a reducing agent if necessary for support. The metal compound, the reducing agent, and the inorganic member or the organic member may be simultaneously added for mixing, and the order of mixing is considered not to particularly influence the production greatly.

3. Method of Producing Compound Using Polymer-Supported Metal Catalyst

For reduction reaction, oxidation reaction, hydrometalation, carbon-carbon bond forming reaction, or carbon-nitrogen bond forming reaction using the polymer-supported metal catalyst, some aspects of the present invention enable smooth proceeding of the reaction and production of a compound in high yield. Further, after the reaction, the catalyst according to some aspects of the present invention is capable of being readily recovered and is confirmed not to cause metal leakage. That is, the catalyst according to some aspects of the present invention is highly active and has a long life to allow repeated use.

<Reduction Reaction>

According to some aspects of the present invention, various types of reduction reaction may be provided using the polymer-supported metal catalyst according to the aspects. Metallic hydrogen complex compounds, metal hydrides, hydrosilanes, borane derivatives, and the like may be used as a reducing agent. The reducing agent, such as alcohols, formic acid, and hydrogen gas, and the like is preferably used, which is readily handled and inexpensive. Hydrogen gas is more preferably used as the reducing agent, which allows easy scaling up and large-scale synthesis. FIG. 1 is a conceptual diagram of an equipment in a flow reaction system. A equipment configured to pass a reactant and hydrogen gas supplied without interruption through the polymer-supported metal catalyst according to some aspects of the present invention fixed to a flow path enables continuous reduction reaction.

According to some aspects of the present invention, hydrogenation reaction to various unsaturated bonds proceeds in relatively mild conditions. Although the reaction proceeds at a reaction temperature approximately at room temperature, the temperature is not particularly limited to around room temperature and may be at lower or higher temperatures. In addition, although the reaction proceeds in a hydrogen gas atmosphere approximately at atmospheric pressure, it may be in a mixed gas atmosphere with an inert gas, such as a nitrogen gas and an argon gas, and the pressure may be appropriately prepared.

<Oxidation Reaction>

Some aspects of the present invention enable various types of oxidation reaction using the polymer-supported metal catalyst according to the aspects. Oxygen gas, peroxide, hypervalence iodic acid, and the like may be used as an oxidant.

According to some aspects of the present invention, Wacker oxidation reaction to various unsaturated bonds proceeds in relatively mild conditions. Although the reaction proceeds at a reaction temperature approximately at room temperature, the temperature is not particularly limited to around room temperature and may be at lower or higher temperatures. In addition, although the reaction proceeds in an oxygen gas atmosphere approximately at atmospheric pressure, it may be in a mixed gas atmosphere with an inert gas, such as a nitrogen gas and an argon gas, and the pressure may be appropriately prepared.

<Carbon-Carbon Bond Forming Reaction>

Some aspects of the present invention enable various types of carbon-carbon bond forming reaction using the polymer-supported metal catalyst according to the aspects and are applicable to various types of reaction, such as cyclopropanation reaction, en reaction, pericyclic reaction, aldol reaction, Michael addition reaction, Sakurai reaction, cross-coupling reaction, and metathesis reaction. Examples of the cross-coupling reaction include Heck reaction, Sonogashira coupling reaction, Suzuki-Miyaura coupling reaction, Kumada coupling reaction, Negishi coupling reaction, Tsuji-Trost reaction, and Stille coupling reaction.

<Carbon-Nitrogen Bond Forming Reaction>

Some aspects of the present invention enable various types of carbon-nitrogen bond forming reaction using the polymer-supported metal catalyst according to the aspects and are applicable to reaction, such as Buchwald-Hartwig cross-coupling reaction and allylation reaction of amine.

<Hydrometalation>

Some aspects of the present invention enable various types of hydrometalation reaction using the polymer-supported metal catalyst according to the aspects and are applicable to reaction, such as hydroboration, hydroalumination, hydrozirconation, hydrostannylation, and hydrosilylation.

EXAMPLES

Specific Examples of the present invention are described below while the present invention is not limited to them.

<Production of Polymer-Supported Metal Catalyst>

A polymer (may be a monomer constituting a polymer) and a reducing agent, as needed, are mixed with a solvent. A transition metal compound is added to the mixed solution and stirred at an appropriate temperature for a certain period of time. An inorganic member (suspension thereof) is then added and further stirred. Methanol is added and further stirred for a while for reprecipitation. Suction filtration and twice of methanol washing are carried out to produce a polymer-supported metal catalyst in powder. Specific examples of a catalyst according to some aspects of the present invention are described with respective details in Examples 1 to 35 below.

TABLE 1

|  | Reducing Agent | Metal Type |
| --- | --- | --- |
| Example 1 | Hydrogen Gas | Palladium (II) Acetate |
| Example 2 | Hydrogen Gas | Palladium (II) Nitrate |
| Example 3 | Hydrogen Gas | Palladium (II) Chloride |
| Example 4 | Hydrogen Gas | Palladium (II) Chloride |
| Example 5 | Hydrogen Gas | Palladium (II) Acetate |
| Example 6 | Sodium Borohydride | Palladium (II) Acetate |
| Example 7 | Sodium Borohydride | Palladium (II) Nitrate |
| Example 8 | Sodium Borohydride | Palladium (II) Chloride |
| Example 9 | Sodium Borohydride | Palladium (II) Chloride |
| Example 10 | Sodium Borohydride | Palladium (II) Acetate |
| Example 11 | Triethylsilane | Palladium (II) Acetate |
| Example 12 | Triethylsilane | Palladium (II) Nitrate |
| Example 13 | Triethylsilane | Palladium (II) Chloride |
| Example 14 | Triethylsilane | Palladium (II) Chloride |
| Example 15 | Triethylsilane | Palladium (II) Acetate |
| Example 16 | PMHS | Palladium (II) Acetate |
| Example 17 | PMHS | Palladium (II) Nitrate |
| Example 18 | PMHS | Palladium (II) Chloride |
| Example 19 | PMHS | Palladium (II) Chloride |
| Example 20 | PMHS | Palladium (II) Acetate |
| Example 21 | PMHS | Hexahydrate Hexachloroplatinate (IV) |
| Example 22 | Triethylsilane | Hexahydrate Hexachloroplatinate (IV) |
| Example 23 | PMHS | Nickel (II) Chloride |
| Example 24 | Triethylsilane | Nickel (II) Chloride |
| Example 25 | PMHS | Ruthenium (III) Chloride |
| Example 26 | Triethylsilane | Ruthenium (III) Chloride |
| Example 27 | PMHS | Rhodium (III) Chloride |

TABLE 1-continued

| | | |
|---|---|---|
| Example 28 | Triethylsilane | Rhodium (III) Chloride |
| Example 29 | PMHS | Tetrachloroaurate (III) Tetrahydrate |
| Example 30 | Triethylsilane | Tetrachloroaurate (III) Tetrahydrate |
| Example 31 | Diphenyl Silane | Palladium (II) Acetate |
| Example 32 | 1,1,3,3-Tetramethyldisiloxane | Palladium (II) Acetate |
| Example 33 | 1,1,3,3-Tetramethyldisiloxane | Palladium (II) Acetate |
| Example 34 | 1,1,3,3-Tetramethyldisiloxane | Palladium (II) Acetate |
| Example 35 | Polysilazane | Palladium (II) Acetate |

| | Polymer or Monomer | Carrier | Name of Catalyst |
|---|---|---|---|
| Example 1 | PDMS | Silicon Oxide | PSiO—Pd/SiO$_2$ |
| Example 2 | PDMS | Titanium Oxide | PSiO—Pd/TiO$_2$ |
| Example 3 | PEI | Zirconium Oxide | PEI-Pd/ZrO$_2$ |
| Example 4 | PDMS | Activated Carbon | PSiO—Pd/C |
| Example 5 | PMPP | Magnesium Oxide | PNCO—Pd/MgO |
| Example 6 | PDMS | Silicon Oxide | PSiO—Pd/SiO$_2$ |
| Example 7 | PDMS | Titanium Oxide | PSiO—Pd/TiO$_2$ |
| Example 8 | PEI | Zirconium Oxide | PEI-Pd/ZrO$_2$ |
| Example 9 | PDMS | Activated Carbon | PSiO—Pd/C |
| Example 10 | PMPP | Magnesium Oxide | PNCO—Pd/MgO |
| Example 11 | PDMS | Silicon Oxide | PSiO—Pd/SiO$_2$ |
| Example 12 | PDMS | Titanium Oxide | PSiO—Pd/TiO$_2$ |
| Example 13 | PEI | Zirconium Oxide | PEI-Pd/ZrO$_2$ |
| Example 14 | PDMS | Activated Carbon | PSiO—Pd/C |
| Example 15 | PMPP | Magnesium Oxide | PNCO—Pd/MgO |
| Example 16 | PMHS | Silicon Oxide | PSiOH—Pd/SiO$_2$ |
| Example 17 | PMHS | Titanium Oxide | PSiOH—Pd/TiO$_2$ |
| Example 18 | PMHS | Zirconium Oxide | PSiOH—Pd/ZrO$_2$ |
| Example 19 | PMHS | Activated Carbon | PSiOH—Pd/C |
| Example 20 | PMHS | Alumina | PSiOH—Pd/Al$_2$O$_3$ |
| Example 21 | PMHS | Alumina | PSiOH—Pt/Al$_2$O$_3$ |
| Example 22 | PDMS | Silicon Oxide | PSiO—Pt/SiO$_2$ |
| Example 23 | PMHS | Alumina | PSiOH—Ni/Al$_2$O$_3$ |
| Example 24 | PDMS | Silicon Oxide | PSiO-Ni/SiO$_2$ |
| Example 25 | PMHS | Alumina | PSiOH—Ru/Al$_2$O$_3$ |
| Example 26 | PDMS | Silicon Oxide | PSiO—Ru/SiO$_2$ |
| Example 27 | PMHS | Alumina | PSiOH—Rh/Al$_2$O$_3$ |
| Example 28 | PDMS | Silicon Oxide | PSiO—Rh/SiO$_2$ |
| Example 29 | PMHS | Alumina | PSiOH—Au/Al$_2$O$_3$ |
| Example 30 | PDMS | Silicon Oxide | PSiO—Au/SiO$_2$ |
| Example 31 | Diphenyl Silane + (R)-(+)-1-Phenylethylamine | Alumina | PSiNPh—Pd/Al$_2$O$_3$ |
| Example 32 | 1,1,3,3-Tetramethyldisiloxane + (R)-(+)-1-Phenylethylamine | Alumina | PSiON—Pd/Al$_2$O$_3$ |
| Example 33 | 1,1,3,3-Tetramethyldisiloxane + Hydroquinone | Alumina | PSiOQ-Pd/Al$_2$O$_3$ |
| Example 34 | 1,1,3,3-Tetramethyldisiloxane + 1,6-Hexanediol | Alumina | PSiOD-Pd/Al$_2$O$_3$ |
| Example 35 | Polysilazane | — | PSiN—Pd |

Example 1

A THF solution containing 250 mg of poly(oxydimethylsilylene) (PDMS) (by Shin-Etsu Chemical Co., Ltd., catalog number: KF-96) is prepared, and 6 mg of palladium (II) acetate (Pd(OAc)$_2$) is added to be stirred in a hydrogen gas (H$_2$) atmosphere at 0° C. for 55 minutes. Subsequently, 1.25 g of silicon oxide (SiO$_2$) is added to be stirred at room temperature for 25 minutes. Methanol is added to be further stirred for 5 minutes for reprecipitation and is subjected to suction filtration and twice of methanol washing to obtain poly(oxydimethylsilylene) and a palladium catalyst (PSiO—Pd/SiO$_2$) in powder supported by silicon oxide.

[Chem. 1]

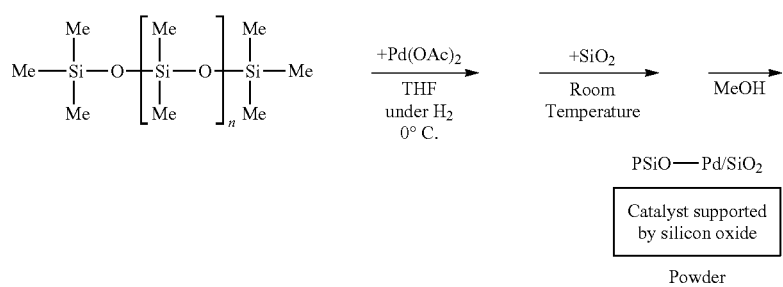

Example 2

A THF solution containing 250 mg of poly(oxydimethylsilylene) is prepared, and 6 mg of palladium (II) nitrate ($Pd(NO_3)_2$) is added to be stirred in a hydrogen gas atmosphere at 0° C. for 55 minutes. Subsequently, 1.25 g of titanium oxide ($TiO_2$) is added to be stirred at room temperature for 25 minutes. Methanol is added to be further stirred for 5 minutes for reprecipitation and is subjected to suction filtration and twice of methanol washing to obtain poly(oxydimethylsilylene) and a palladium catalyst (PSiO—$Pd/TiO_2$) in powder supported by titanium oxide.

[Chem. 2]

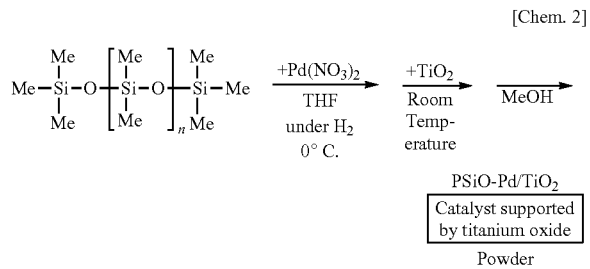

Example 3

A THF solution containing 250 mg of polyethyleneimine (PEI) (by Wako Pure Chemical Industries, Ltd., catalog number: 167-1195) is prepared, and 6 mg of palladium (II) chloride ($PdCl_2$) is added to be stirred in a hydrogen gas atmosphere at 0° C. for 55 minutes. Subsequently, 1.25 g of zirconium oxide ($ZrO_2$) is added to be stirred at room temperature for 25 minutes. Methanol is added to be further stirred for 5 minutes for reprecipitation and is subjected to suction filtration and twice of methanol washing to obtain polyethyleneimine and a palladium catalyst (PEI-Pd/$ZrO_2$) in powder supported by zirconium oxide.

[Chem. 3]

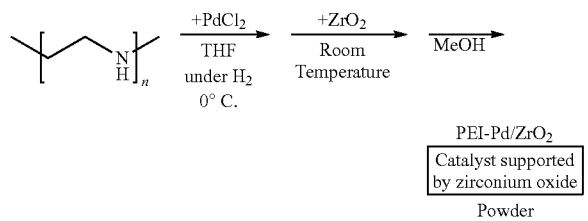

Example 4

A THF solution containing 250 mg of poly(oxydimethylsilylene) is prepared, and 6 mg of palladium (II) chloride is added to be stirred in a hydrogen gas atmosphere at 0° C. for 55 minutes. Subsequently, 1.25 g of activated carbon is added to be stirred at room temperature for 25 minutes. Methanol is added to be further stirred for 5 minutes for reprecipitation and is subjected to suction filtration and twice of methanol washing to obtain poly(oxydimethylsilylene) and a palladium catalyst (PSiO—Pd/C) in powder supported by activated carbon.

[Chem. 4]

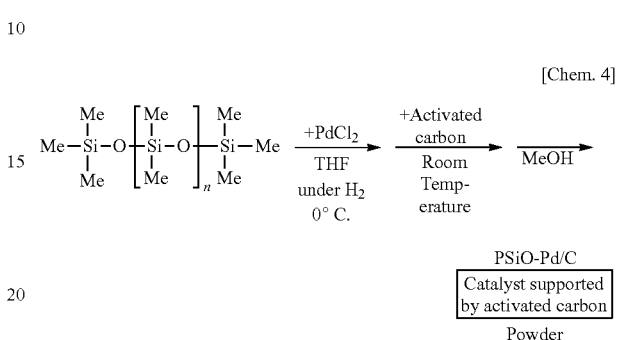

Example 5

A THF solution containing 250 mg of polymethylene phenylene isocyanate (PMPP) (by Sigma-Aldrich Co. LLC., catalog number 406597) is prepared, and 6 mg of palladium (II) acetate is added to be stirred in a hydrogen gas atmosphere at 0° C. for 55 minutes. Subsequently, 1.25 g of magnesium oxide (MgO) is added to be stirred at room temperature for 25 minutes. Methanol is added to be further stirred for 5 minutes for reprecipitation and is subjected to suction filtration and twice of methanol washing to obtain polymethylene phenylene isocyanate and a palladium catalyst (PNCO—Pd/MgO) in powder supported by magnesium oxide.

[Chem. 5]

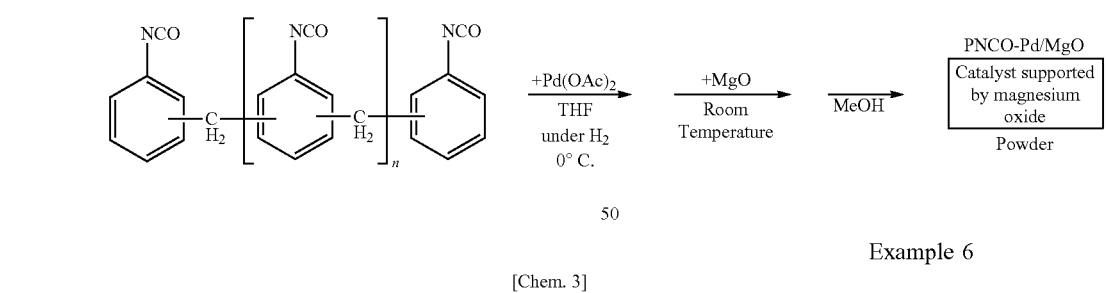

Example 6

A THF suspension containing 250 mg of poly(oxydimethylsilylene) and 5 mg of sodium borohydride ($NaBH_4$) is prepared, and 6 mg of palladium (II) acetate is added to be stirred at 0° C. for 55 minutes. Subsequently, 1.25 g of silicon oxide is added to be stirred at room temperature for 25 minutes. Methanol is added to be further stirred for 5 minutes for reprecipitation and is subjected to suction filtration and twice of methanol washing to obtain poly(oxydimethylsilylene) and a palladium catalyst (PSiO—Pd/$SiO_2$) in powder supported by silicon oxide.

[Chem. 6]

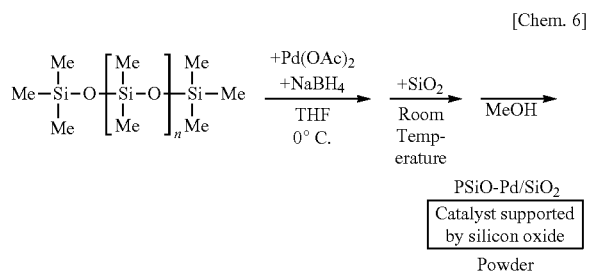

Example 7

A THF suspension containing 250 mg of poly(oxydimethylsilylene) and 5 mg of sodium borohydride is prepared, and 6 mg of palladium (II) nitrate is added to be stirred at 0° C. for 55 minutes. Subsequently, 1.25 g of titanium oxide is added to be stirred at room temperature for 25 minutes. Methanol is added to be further stirred for 5 minutes for reprecipitation and is subjected to suction filtration and twice of methanol washing to obtain poly(oxydimethylsilylene) and a palladium catalyst (PSiO—Pd/TiO$_2$) in powder supported by titanium oxide.

[Chem. 7]

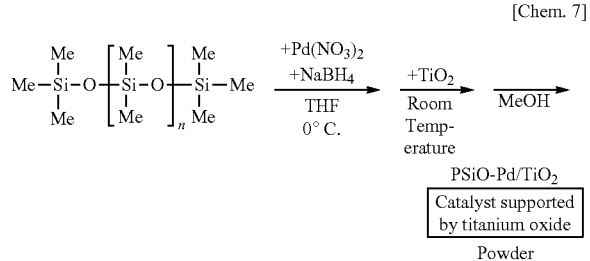

Example 8

A THF suspension containing 250 mg of polyethyleneimine and 5 mg of sodium borohydride is prepared, and 6 mg of palladium (II) chloride is added to be stirred at 0° C. for 55 minutes. Subsequently, 1.25 g of zirconium oxide is added to be stirred at room temperature for 25 minutes. Methanol is added to be further stirred for 5 minutes for reprecipitation and is subjected to suction filtration and twice of methanol washing to obtain polyethyleneimine and a palladium catalyst (PEI-Pd/ZrO$_2$) in powder supported by zirconium oxide.

[Chem. 8]

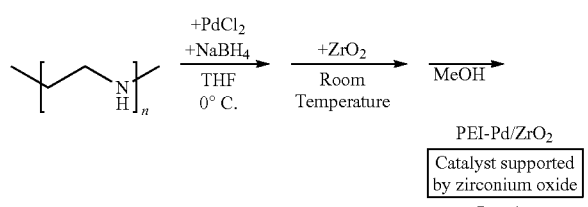

Example 9

A THF suspension containing 250 mg of poly(oxydimethylsilylene) and 5 mg of sodium borohydride is prepared, and 6 mg of palladium (II) chloride is added to be stirred at 0° C. for 55 minutes. Subsequently, 1.25 g of activated carbon is added to be stirred at room temperature for 25 minutes. Methanol is added to be further stirred for 5 minutes for reprecipitation and is subjected to suction filtration and twice of methanol washing to obtain poly(oxydimethylsilylene) and a palladium catalyst (PSiO—Pd/C) in powder supported by activated carbon.

[Chem. 9]

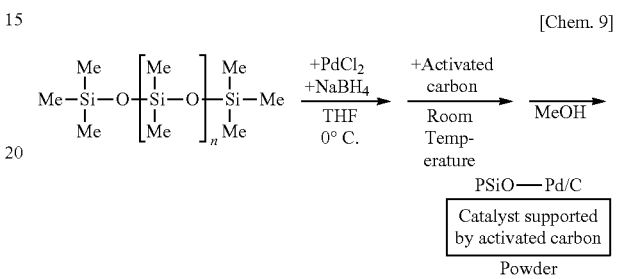

Example 10

A THF suspension containing 250 mg of polymethylene phenylene isocyanate and 5 mg of sodium borohydride is prepared, and 6 mg of palladium (II) acetate is added to be stirred at 0° C. for 55 minutes. Subsequently, 1.25 g of magnesium oxide is added to be stirred at room temperature for 25 minutes. Methanol is added to be further stirred for 5 minutes for reprecipitation and is subjected to suction filtration and twice of methanol washing to obtain polymethylene phenylene isocyanate and a palladium catalyst (PNCO—Pd/MgO) in powder supported by magnesium oxide.

[Chem. 10]

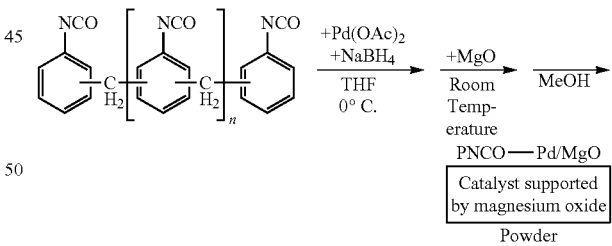

Example 11

A THF solution containing 250 mg of poly(oxydimethylsilylene) and 16 mg of triethylsilane (Et$_3$SiH) is prepared, and 6 mg of palladium (II) acetate is added to be stirred at 0° C. for 55 minutes. Subsequently, 1.25 g of silicon oxide is added to be stirred at room temperature for 25 minutes. Methanol is added to be further stirred for 5 minutes for reprecipitation and is subjected to suction filtration and twice of methanol washing to obtain poly(oxydimethylsilylene) and a palladium catalyst (PSiO—Pd/SiO$_2$) in powder supported by silicon oxide.

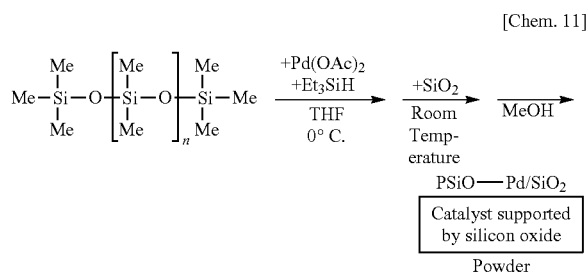

Example 12

A THF solution containing 250 mg of poly(oxydimethylsilylene) and 16 mg of triethylsilane is prepared, and 6 mg of palladium (II) nitrate is added to be stirred at 0° C. for 55 minutes. Subsequently, 1.25 g of titanium oxide is added to be stirred at room temperature for 25 minutes. Methanol is added to be further stirred for 5 minutes for reprecipitation and is subjected to suction filtration and twice of methanol washing to obtain poly(oxydimethylsilylene) and a palladium catalyst (PSiO—Pd/TiO$_2$) in powder supported by titanium oxide.

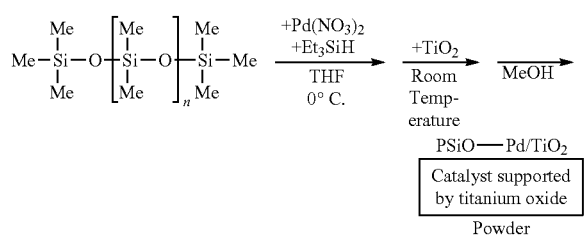

Example 13

A THF solution containing 250 mg of polyethyleneimine and 16 mg of triethylsilane is prepared, and 6 mg of palladium (II) chloride is added to be stirred at 0° C. for 55 minutes. Subsequently, 1.25 g of zirconium oxide is added to be stirred at room temperature for 25 minutes. Methanol is added to be further stirred for 5 minutes for reprecipitation and is subjected to suction filtration and twice of methanol washing to obtain polyethyleneimine and a palladium catalyst (PEI-Pd/ZrO$_2$) in powder supported by zirconium oxide.

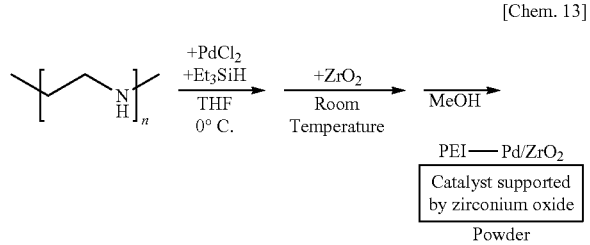

Example 14

A THF solution containing 250 mg of poly(oxydimethylsilylene) (PDMS) and 16 mg of triethylsilane is prepared, and 6 mg of palladium (II) chloride is added to be stirred at 0° C. for 55 minutes. Subsequently, 1.25 g of activated carbon is added to be stirred at room temperature for 25 minutes. Methanol is added to be further stirred for 5 minutes for reprecipitation and is subjected to suction filtration and twice of methanol washing to obtain poly(oxydimethylsilylene) and a palladium catalyst (PSiO—Pd/C) in powder supported by activated carbon.

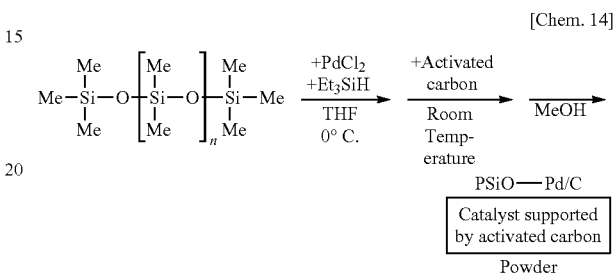

Example 15

A THF solution containing 250 mg of polymethylene phenylene isocyanate and 16 mg of triethylsilane is prepared, and 6 mg of palladium (II) acetate is added to be stirred at 0° C. for 55 minutes. Subsequently, 1.25 g of magnesium oxide is added to be stirred at room temperature for 25 minutes. Methanol is added to be further stirred for 5 minutes for reprecipitation and is subjected to suction filtration and twice of methanol washing to obtain polymethylene phenylene isocyanate and a palladium catalyst (PNCO—Pd/MgO) in powder supported by magnesium oxide.

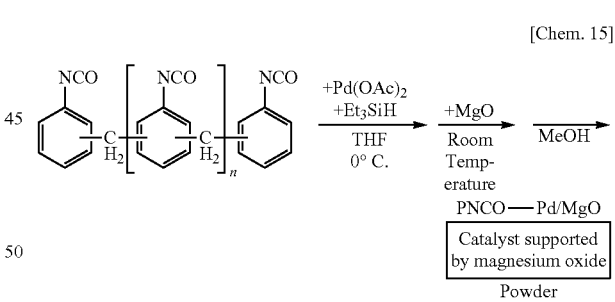

Example 16

A THF solution containing 250 mg of poly(oxydimethylsilylene) (oxymethylhydrosilylene (PMHS)) (by Shin-Etsu Chemical Co., Ltd., catalog number KF-99) is prepared, and 6 mg of palladium (II) acetate is added to be stirred at 0° C. for 55 minutes. Subsequently, 1.25 g of silicon oxide is added to be stirred at room temperature for 25 minutes. Methanol is added to be further stirred for 5 minutes for reprecipitation and is subjected to suction filtration and twice of methanol washing to obtain a palladium catalyst (PSiOH—Pd/SiO$_2$) in powder supported by silicon oxide.

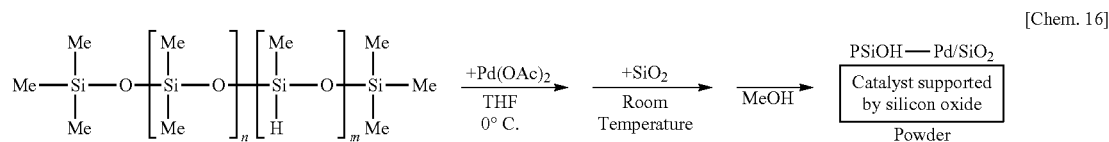

[Chem. 16]

Example 17

A THF solution containing 250 mg of poly(oxydimethylsilylene) (oxymethylhydrosilylene) is prepared, and 6 mg of palladium (II) nitrate is added to be stirred at 0° C. for 55 minutes. Subsequently, 1.25 g of titanium oxide is added to be stirred at room temperature for 25 minutes. Methanol is added to be further stirred for 5 minutes for reprecipitation and is subjected to suction filtration and twice of methanol washing to obtain a palladium catalyst (PSiOH—Pd/TiO$_2$) in powder supported by titanium oxide.

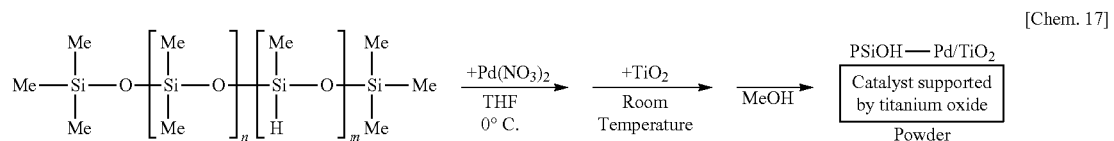

[Chem. 17]

Example 18

A THF solution containing 250 mg of poly(oxydimethylsilylene) (oxymethylhydrosilylene) is prepared, and 6 mg of palladium (II) chloride is added to be stirred at 0° C. for 55 minutes. Subsequently, 1.25 g of zirconium oxide is added to be stirred at room temperature for 25 minutes. Methanol is added to be further stirred for 5 minutes for reprecipitation and is subjected to suction filtration and twice of methanol washing to obtain a palladium catalyst (PSiOH—Pd/ZrO$_2$) in powder supported by zirconium oxide.

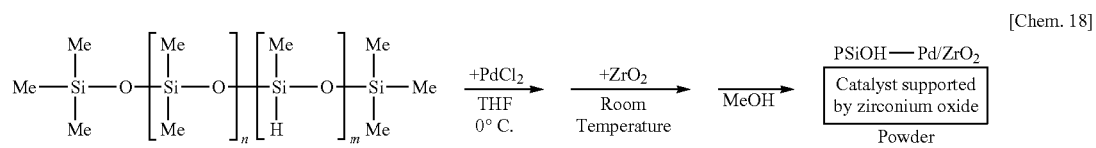

[Chem. 18]

Example 19

A THF solution containing 250 mg of poly(oxydimethylsilylene) (oxymethylhydrosilylene) is prepared, and 6 mg of palladium (II) chloride is added to be stirred at 0° C. for 55 minutes. Subsequently, 1.25 g of activated carbon is added to be stirred at room temperature for 25 minutes. Methanol is added to be further stirred for 5 minutes for reprecipitation and is subjected to suction filtration and twice of methanol washing to obtain a palladium catalyst (PSiOH—Pd/C) in powder supported by activated carbon.

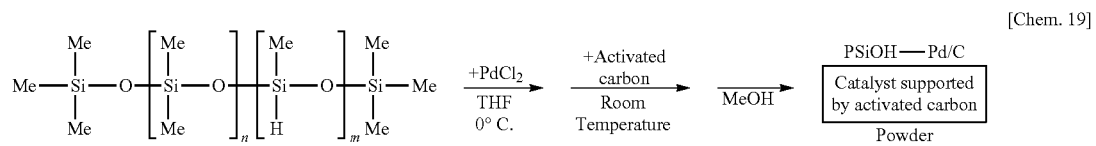

[Chem. 19]

Example 20

A THF solution containing 250 mg of poly(oxydimethylsilylene) (oxymethylhydrosilylene) is prepared, and 6 mg of palladium (II) acetate is added to be stirred at 0° C. for 55 minutes. Subsequently, 1.25 g of alumina (Al$_2$O$_3$) is added to be stirred at room temperature for 25 minutes. Methanol is added to be further stirred for 5 minutes for reprecipitation and is subjected to suction filtration and twice of methanol washing to obtain a palladium catalyst (PSiOH—Pd/Al$_2$O$_3$) in powder supported by alumina.

[Chem. 20]

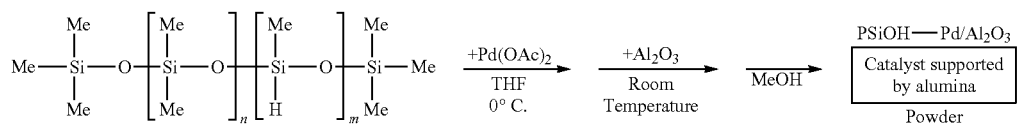

Example 21

A toluene suspension containing 250 mg of poly(oxydimethylsilylene) (oxymethylhydrosilylene) and 1.25 g of alumina is prepared, and 6 mg of hexahydrate hexachloroplatinate (IV) (H$_2$PtCl$_6$.6(H$_2$O)) is added to be stirred at room temperature for 14 hours. Methanol is added to be further stirred for 5 hours for reprecipitation and is subjected to suction filtration and twice of methanol washing to obtain a platinum catalyst (PSiOH—Pt/Al$_2$O$_3$) in powder supported by alumina.

[Chem. 21]

Example 22

A toluene suspension containing 250 mg of poly(oxydimethylsilylene), 16 mg of triethylsilane, and 1.25 g of silicon oxide is prepared, and 6 mg of hexahydrate hexachloroplatinate (IV) is added to be stirred at room temperature for 14 hours. Methanol is added to be further stirred for 5 hours for reprecipitation and is subjected to suction filtration and twice of methanol washing to obtain a platinum catalyst (PSiO—Pt/SiO$_2$) in powder supported by silicon oxide.

[Chem. 22]

Example 23

A THF suspension containing 250 mg of poly(oxydimethylsilylene) (oxymethylhydrosilylene) and 1.25 g of alumina is prepared, and 6 mg of nickel (II) chloride (NiCl$_2$) is added to be stirred at room temperature for 14 hours. Methanol is added to be further stirred for 5 hours for reprecipitation and is subjected to suction filtration and twice of methanol washing to obtain a nickel catalyst (PSiOH—Ni/Al$_2$O$_3$) in powder supported by alumina.

[Chem. 23]

-continued

Example 24

A THF suspension containing 250 mg of poly(oxydimethylsilylene), 16 mg of triethylsilane, and 1.25 g of silicon oxide is prepared, and 6 mg of nickel (II) chloride is added to be stirred at room temperature for 14 hours. Methanol is added to be further stirred for 5 hours for reprecipitation and is subjected to suction filtration and twice of methanol washing to obtain a nickel catalyst (PSiO—Ni/SiO$_2$) in powder supported by silicon oxide.

[Chem. 24]

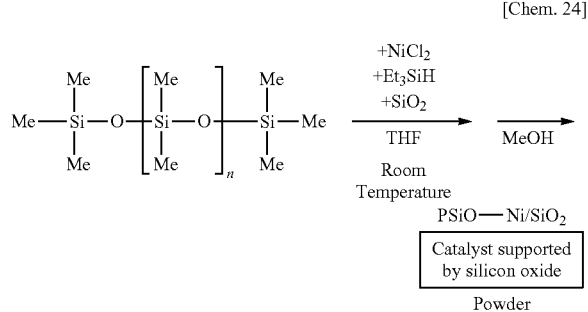

Example 25

A THF suspension containing 250 mg of poly(oxydimethylsilylene) (oxymethylhydrosilylene) and 1.25 g of alumina is prepared, and 6 mg of ruthenium (III) chloride ($RuCl_3$) is added to be stirred at room temperature for 14 hours. Methanol is added to be further stirred for 5 hours for reprecipitation and is subjected to suction filtration and twice of methanol washing to obtain a ruthenium catalyst ($PSiOH-Ru/Al_2O_3$) in powder supported by alumina.

[Chem. 25]

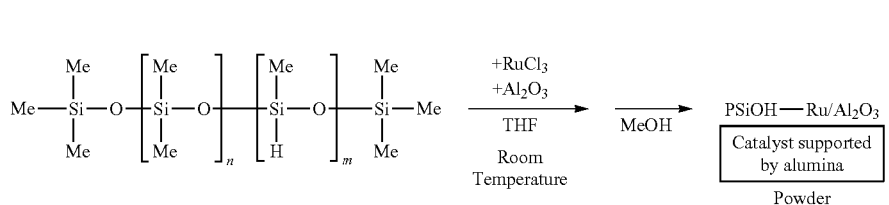

Example 26

A THF suspension containing 250 mg of poly(oxydimethylsilylene), 16 mg of triethylsilane, and 1.25 g of silicon oxide is prepared, and 6 mg of ruthenium (III) chloride is added to be stirred at room temperature for 14 hours. Methanol is added to be further stirred for 5 hours for reprecipitation and is subjected to suction filtration and twice of methanol washing to obtain a ruthenium catalyst ($PSiO-Ru/SiO_2$) in powder supported by silicon oxide.

[Chem. 26]

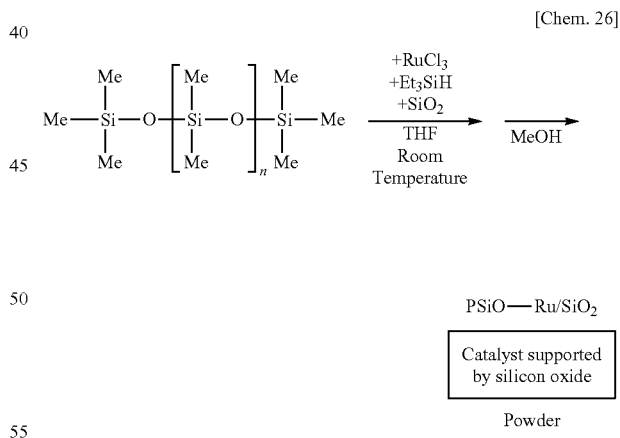

Example 27

A THF suspension containing 250 mg of poly(oxydimethylsilylene) (oxymethylhydrosilylene) and 1.25 g of alumina is prepared, and 6 mg of rhodium (III) chloride ($RhCl_3$) is added to be stirred at room temperature for 14 hours. Methanol is added to be further stirred for 5 hours for reprecipitation and is subjected to suction filtration and twice of methanol washing to obtain poly(oxydimethylsilylene) (oxymethylhydrosilylene) and a rhodium catalyst ($PSiOH-Rh/Al_2O_3$) in powder supported by alumina.

[Chem. 27]

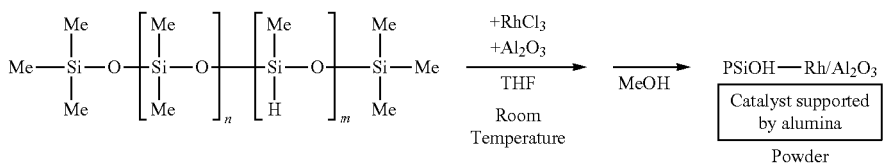

Example 28

A THF suspension containing 250 mg of poly(oxydimethylsilylene), 16 mg of triethylsilane, and 1.25 g of silicon oxide is prepared, and 6 mg of rhodium (III) chloride is added to be stirred at room temperature for 14 hours. Methanol is added to be further stirred for 5 hours for reprecipitation and is subjected to suction filtration and twice of methanol washing to obtain a rhodium catalyst (PSiO—Rh/SiO$_2$) in powder supported by silicon oxide.

Example 30

A THF suspension containing 250 mg of poly(oxydimethylsilylene), 16 mg of triethylsilane, and 1.25 g of silicon oxide is prepared, and 6 mg of tetrachloroaurate (III) tetrahydrate is added to be stirred at room temperature for 14 hours. Methanol is added to be further stirred for 5 hours for reprecipitation and is subjected to suction filtration and twice of methanol washing to obtain a gold catalyst (PSiO—Au/SiO$_2$) in powder supported by silicon oxide.

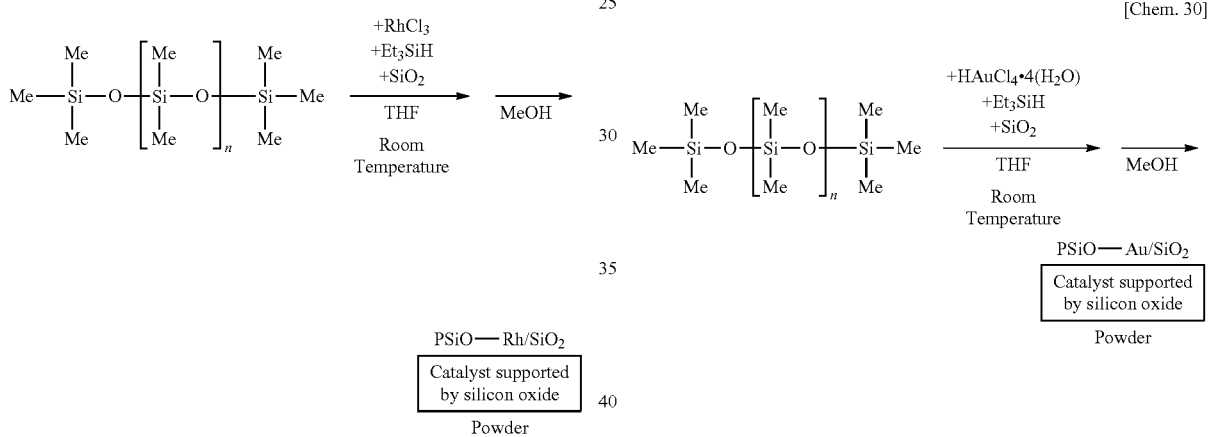

[Chem. 28]

[Chem. 30]

Example 29

A THF suspension containing 250 mg of poly(oxydimethylsilylene) (oxymethylhydrosilylene) and 1.25 g of alumina is prepared, and 6 mg of tetrachloroaurate (III) tetrahydrate (HAuCl$_4$·4(H$_2$O)) is added to be stirred at room temperature for 14 hours. Methanol is added to be further stirred for 5 hours for reprecipitation and is subjected to suction filtration and twice of methanol washing to obtain a gold catalyst (PSiOH—Au/Al$_2$O$_3$) in powder supported by alumina.

Example 31

A chloroform solution containing 20.0 mg of diphenylsilane and 13.0 mg of (R)-(+)-1-phenylethylamine, which is a chiral compound, is prepared, and 10 mg of palladium (II) acetate is added to be stirred at room temperature for 30 minutes. Subsequently, 165 mg of alumina is added to be stirred at room temperature for 10 minutes. Methanol is added to be further stirred for 10 minutes for reprecipitation and is subjected to suction filtration and twice of methanol washing to obtain a palladium catalyst (PSiN—Pd/Al$_2$O$_3$) in gray powder supported by alumina.

[Chem. 29]

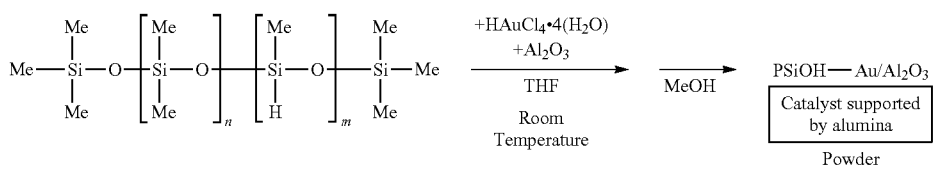

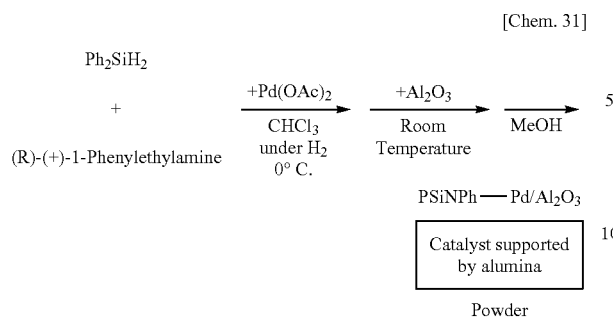

Example 32

A THF solution containing 100 mg of 1,1,3,3-tetramethyldisiloxane and 90 mg of (R)-(+)-1-phenylethylamine as chiral amine is prepared, and 7 mg of palladium (II) acetate is added to be stirred at 0° C. for 30 minutes. Subsequently, 1.5 g of alumina is added to be stirred at room temperature for 1 hour. Methanol is added to be further stirred for 10 minutes for reprecipitation and is subjected to suction filtration and twice of methanol washing to obtain a palladium catalyst (PSiON—Pd/$Al_2O_3$) in gray powder supported by alumina. The catalyst includes at least two elements, such as an oxygen atom and a nitrogen atom, for example, having an electronegativity higher than an electronegativity of a hydrogen atom. According to EDX measurement results, the respective composition ratios of aluminum atoms, silicon atoms, and palladium atoms are 97.446, 2.030, and 0.134.

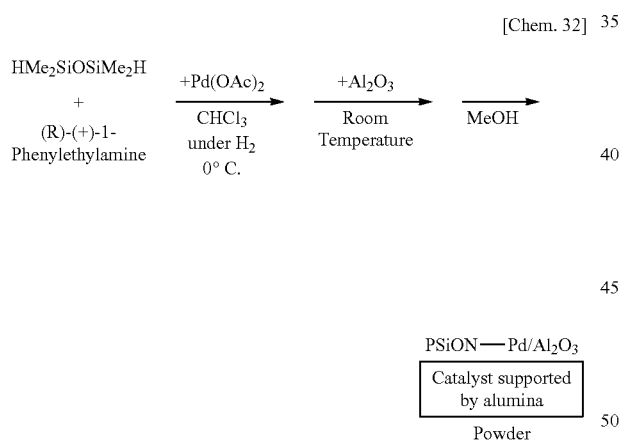

Example 33

A THF solution containing 20 mg of 1,1,3,3-tetramethyldisiloxane and 20 mg of hydroquinone is prepared, and 2 mg of palladium (II) acetate is added to be stirred at 0° C. for 30 minutes. Subsequently, 380 mg of alumina is added to be stirred at room temperature for 35 minutes. Methanol is added to be further stirred for 10 minutes for reprecipitation and is subjected to suction filtration and twice of methanol washing to obtain a palladium catalyst (PSiOQ-Pd/$Al_2O_3$) in gray powder supported by alumina. According to EDX measurement results, the respective composition ratios of aluminum atoms, silicon atoms, and palladium atoms are 97.864, 1.634, and 0.163.

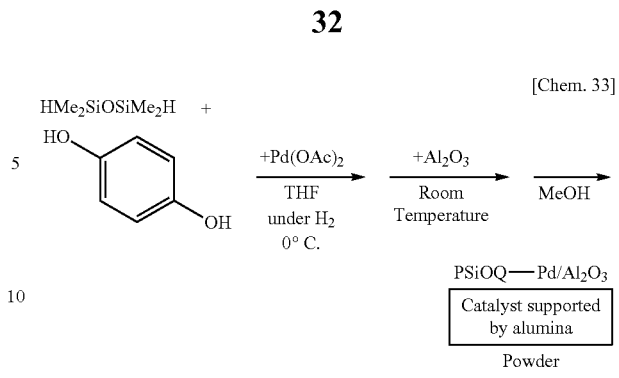

Example 34

A THF solution containing 50 mg of 1,1,3,3-tetramethyldisiloxane and 44 mg of 1,6-hexanediol is prepared, and 3 mg of palladium (II) acetate is added to be stirred at 0° C. for 55 minutes. Subsequently, 380 mg of alumina is added to be stirred at room temperature for 1 hour. Methanol is added to be further stirred for 5 minutes for reprecipitation and is subjected to suction filtration and twice of methanol washing to obtain a palladium catalyst (PSiOD-Pd/$Al_2O_3$) in gray powder supported by alumina.

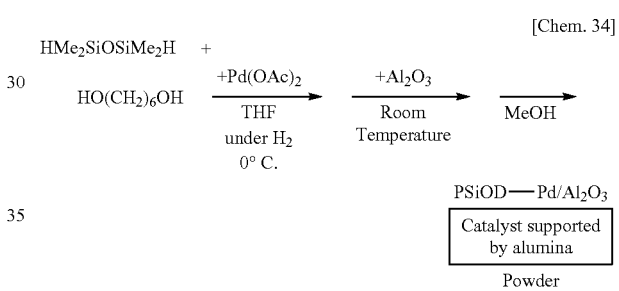

Example 35

A THF solution containing 100 mg of polysilazane is prepared, and 34 mg of palladium (II) acetate is added to be stirred in reflux conditions for 2 hours. Methanol is added to be further stirred for 5 minutes for reprecipitation and is subjected to suction filtration and twice of methanol washing to obtain a palladium catalyst (PSiN—Pd) in black powder.

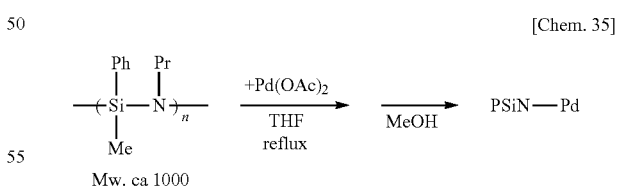

<Production of Compound Using Polymer-Supported Metal Catalyst>

Using some of the synthesized metal catalysts, high catalytic activity is exhibited in some chemical reactions. The catalyst is recovered after termination of reaction, and metal leakage is checked to be found that any catalyst had almost no leakage and the polymer had high retentivity. In some of the catalysts, no metal leakage at all is confirmed by the employed method, resulting in obtaining the catalysts with extremely high durability.

[Method of Confirming Metal Leakage]

The solution after reaction is filtered by a syringe filter, followed by measuring the filtrate by EDX to detect leakage of the catalyst.

[Reduction Reaction Using Polymer-Supported Palladium Catalyst]

A hexane solution containing a substrate of 1.0 mmol is prepared, and 10 mg of a palladium catalyst is added to make a suspension and to be stirred in a hydrogen gas atmosphere at 1 atmospheric pressure at room temperature for several hours. The palladium catalyst is then removed from the suspension by filtration. Subsequently, the filtrate is concentrated for purification by column chromatography to obtain a corresponding reductant. Results of Examples 36 to 50 and Comparative Examples 1 to 3 are shown in Table 2. (In Examples 46 to 50 and Comparative Example 3, THF is used for the solvent instead of hexane.)

TABLE 2

| | Substrate | Catalyst | Yield (%) | Pd Leakage * |
|---|---|---|---|---|
| Example 36 | Ethyl Cinnamate | PSiOH—Pd/Al$_2$O$_3$ | 100 | ⊙ |
| Example 37 | | PSiO—Pd/TiO$_2$ | 97 | ○ |
| Example 38 | | PNCO—Pd/MgO | 95 | ○ |
| Example 39 | | PEI-Pd/ZrO$_2$ | 92 | ○ |
| Example 40 | | PSiON—Pd/Al$_2$O$_3$ | 100 | ○ |
| Comparative Example 1 | | Pd/C | 99 | X |
| Example 41 | Diphenylacety-lene | PSiOH—Pd/Al$_2$O$_3$ | 92 | ⊙ |
| Example 42 | | PSiO—Pd/TiO$_2$ | 85 | ⊙ |
| Example 43 | | PNCO—Pd/MgO | 82 | ○ |
| Example 44 | | PEI-Pd/ZrO$_2$ | 80 | ○ |
| Example 45 | | PSiON—Pd/Al$_2$O$_3$ | 93 | ○ |
| Comparative Example 2 | | Pd/C | 93 | X |
| Example 46 | Nitrobenzene | PSiOH—Pd/Al$_2$O$_3$ | 88 | ⊙ |
| Example 47 | | PSiO—Pd/TiO$_2$ | 84 | ○ |
| Example 48 | | PNCO—Pd/MgO | 82 | ○ |
| Example 49 | | PEI-Pd/ZrO$_2$ | 84 | ○ |
| Example 50 | | PSiON—Pd/Al$_2$O$_3$ | 84 | ○ |
| Comparative Example 3 | | Pd/C | 89 | X |

* Pd Leakage
Not Found at All –> ⊙
Found Very Trace Amount –> ○
Found Trace Amount –> Δ
Found Substantial Amount –> X As shown in Examples 36 to 40, in reduction reaction to ethyl cinnamate, the reaction smoothly proceeded and the corresponding reductant is obtained in high yield. Using a palladium catalyst supported by a polymer according to some aspects of the present invention, almost no palladium is detected from the filtrate obtained by removing the palladium catalyst from the suspension after reaction. Particularly using PSiOH—Pd/Al$_2$O$_3$, it is not at all detected, resulting in high supporting power. In contrast, in Comparative Example 1 using Pd/C not supported by the polymer, a substantial amount of palladium leakage is confirmed.

As shown in Examples 41 to 45, in reduction reaction to diphenylacetylene, the reaction smoothly proceeded and the corresponding reductant is obtained in high yield. At this point, one hydrogen molecule is added to one acetylene molecule, and cis-stilbene is chemoselectively and stereoselectively obtained as a product. Using a palladium catalyst supported by a polymer according to some aspects of the present invention, almost no palladium is detected from the filtrate obtained by removing the palladium catalyst from the suspension after reaction. Particularly, using PSiOH—Pd/Al$_2$O$_3$, it is not at all detected, resulting in high supporting power. In contrast, in Comparative Example 2 using Pd/C not supported by the polymer, a substantial amount of palladium leakage is confirmed.

As shown in Examples 46 to 50, reduction reaction proceeded even to nitrobenzene having a nitro group, and amine as the corresponding reductant is obtained in high yield. Using a palladium catalyst supported by a polymer according to some aspects of the present invention, almost no palladium is detected from the filtrate obtained by removing the palladium catalyst from the suspension after reaction. Particularly, using PSiOH—Pd/Al$_2$O$_3$, it is not at all detected, resulting in high supporting power. In contrast, in Comparative Example 3 using Pd/C not supported by the polymer, a substantial amount of palladium leakage is confirmed.

[Hydrogenation Reaction Using Polymer-Supported Platinum Catalyst]

A hexane solution containing 1.0 mmol of diphenylacetylene is prepared and 0.05 mmol of a platinum catalyst is added to make a suspension and to be stirred in a hydrogen gas atmosphere at 1 atmospheric pressure at room temperature for several hours. The platinum catalyst is then removed from the suspension by filtration. Subsequently, the filtrate is concentrated for purification by column chromatography to obtain bibenzyl as a product in which two hydrogen molecules are added to diphenylacetylene.

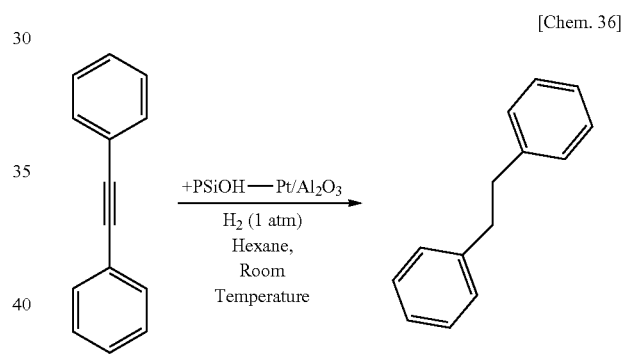

[Chem. 36]

[Carbon-Carbon Bond Forming Reaction Using Polymer-Supported Metal Catalyst]

(Heck Reaction)

A toluene (PhMe) solution containing 1.0 mmol of iodobenzene (A), 1.1 mmol of acrylic acid (B) and 1.5 mmol of triethylamine (NEt$_3$) is prepared and 0.05 mmol of a palladium catalyst is added to be stirred in heating reflux conditions for several hours. Dichloromethane is then added, and the palladium catalyst is removed from the suspension by filtration. Subsequently, the filtrate is concentrated for purification by column chromatography to obtain trans-cinnamic acid (C), which is a corresponding coupling body, in a white solid. Results are shown in Examples 51 to 54 Table 3.

As shown in Example 55, instead of iodobenzene and acrylic acid, 1.5 mmol of 3,5-dimethoxy iodobenzene (D) and 3.0 mmol of 4-acetoxystyrene (E) are used respectively to obtain trans-4-acetoxy-3'-5'-dimethoxy stilbene (F) in a white solid.

As shown in Examples 51 to 55, in Heck reaction using aryl halide and olefin as raw materials, the reaction smoothly proceeded and corresponding aryl olefin is obtained. Using a palladium catalyst supported by a polymer according to some aspects of the present invention, almost no palladium is detected from the filtrate obtained by removing the palladium catalyst from the suspension after reaction. Particularly, using PSiOH—Pd/Al$_2$O$_3$, no palladium at all is detected from the filtrate by measurement using EDX (energy dispersive x-ray spectroscopy). This shows that PSiOH—Pd/Al$_2$O$_3$ had high palladium supporting power. In contrast, in Comparative Example 4 using Pd/C not supported by the polymer, a substantial amount of palladium leakage is confirmed.

[Chem. 37]

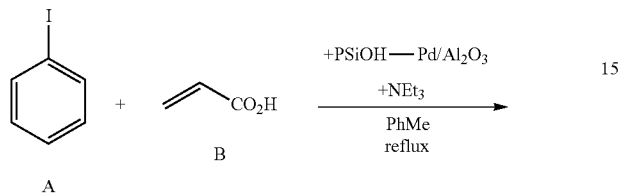

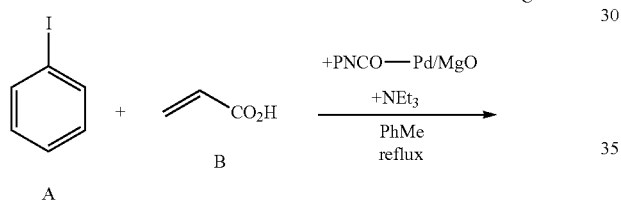

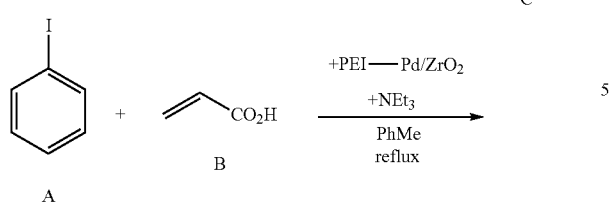

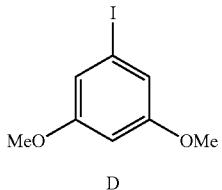

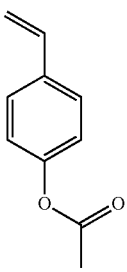

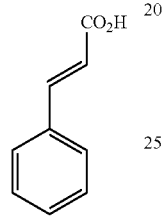

(Sonogashira Coupling Reaction)

A dimethylformamide (DMF) solution containing 1.0 mmol of iodobenzene (A), 1.5 mmol of phenyl acetylene (G), and 1.5 mmol of triethylamine (NEt$_3$) is prepared, and 0.05 mmol of a palladium catalyst and 0.05 mmol of copper iodide (CuI) are added to be stirred at 90° C. for several hours. The palladium catalyst is then removed from the suspension by filtration. Subsequently, the filtrate is concentrated for purification by column chromatography to obtain diphenylacetylene (H), which is a corresponding coupling body, in a white solid. Results of Examples 56 to 59 and Comparative Example 5 are shown in Table 3.

As shown in Examples 56 to 59, in coupling reaction using iodobenzene (A) and phenyl acetylene (G) as raw materials, the reaction smoothly proceeded and diphenylacetylene (H) is obtained in high yield. Using a palladium catalyst supported by a polymer according to some aspects of the present invention, almost no palladium is detected from the filtrate obtained by removing the palladium catalyst from the suspension after reaction. Particularly using PSiOH—Pd/Al$_2$O$_3$, no palladium at all is detected from the filtrate by measurement using EDX (energy dispersive x-ray spectroscopy). This indicates that PSiOH—Pd/Al$_2$O$_3$ had high palladium supporting power. In contrast, in Comparative Example 5 using Pd/C not supported by the polymer, a substantial amount of palladium leakage is confirmed.

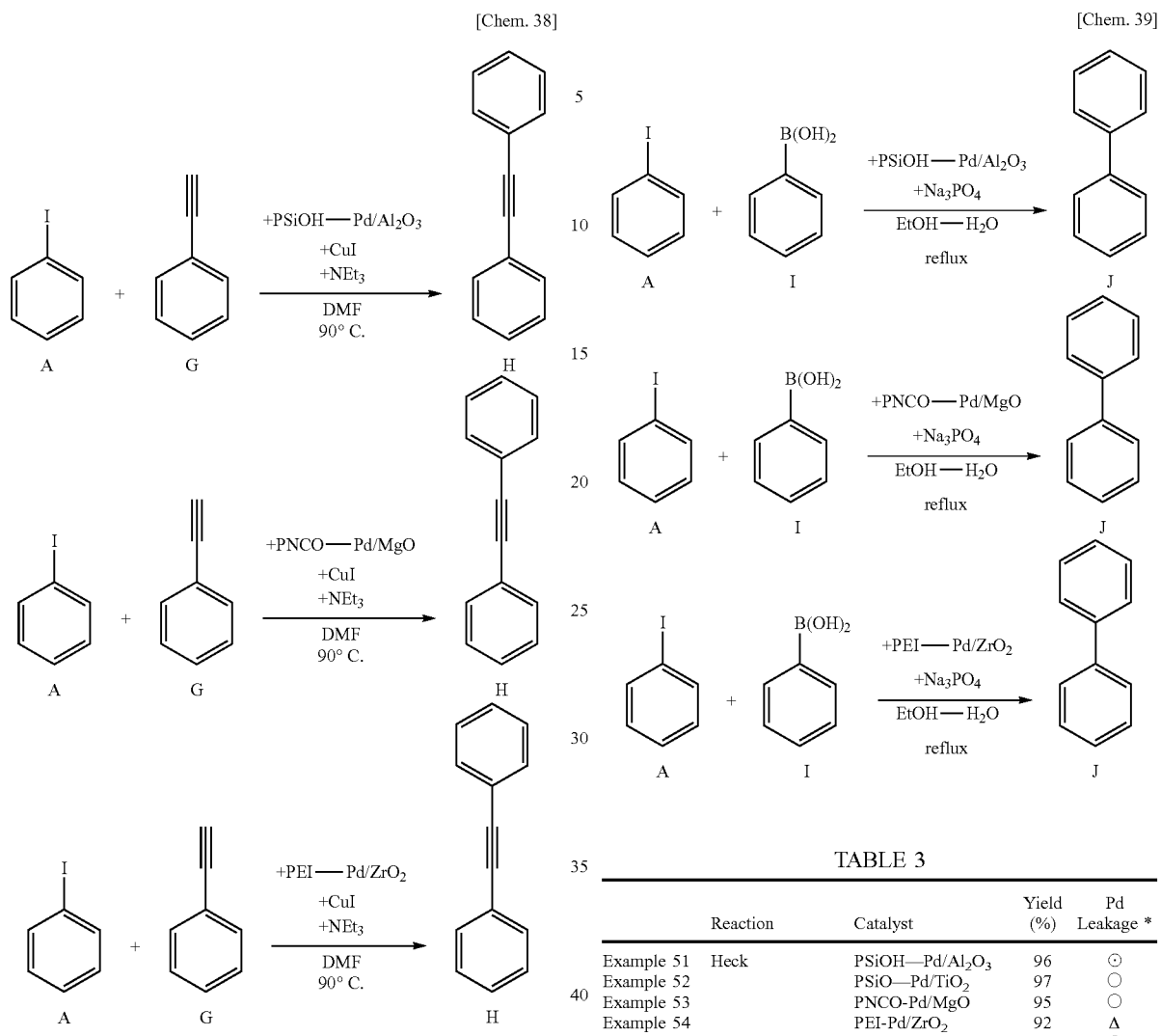

(Suzuki-Miyaura Coupling Reaction)

An aqueous 40% ethanol solution (EtOH—H$_2$O) containing 1.0 mmol of iodobenzene (A), 1.5 mmol of phenylboronic acid (I), and 3.0 mmol of sodium phosphate (Na$_3$PO$_4$) is prepared, and 0.05 mmol of a palladium catalyst is added to be stirred in heating reflux conditions for several hours. The palladium catalyst is then removed from the suspension by filtration. Subsequently, the filtrate is concentrated for purification by column chromatography to obtain biphenyl (J), which is a corresponding coupling body, in a white solid. Results of Examples 60 to 63 and Comparative Example 6 are shown in Table 3.

As shown in Examples 60 to 63, in Suzuki-Miyaura coupling reaction using iodobenzene (A) and phenylboronic acid (I) as raw materials, the reaction smoothly proceeded and biphenyl (J) is obtained in high yield. Using a palladium catalyst supported by a polymer according to some aspects of the present invention, almost no palladium is detected from the filtrate obtained by removing the palladium catalyst from the suspension after reaction. Particularly, using PSiOH—Pd/Al$_2$O$_3$, no palladium at all is detected from the filtrate by measurement using EDX (energy dispersive x-ray spectroscopy). This indicates that PSiOH—Pd/Al$_2$O$_3$ had high palladium supporting power.

TABLE 3

| | Reaction | Catalyst | Yield (%) | Pd Leakage * |
|---|---|---|---|---|
| Example 51 | Heck | PSiOH—Pd/Al$_2$O$_3$ | 96 | ⊙ |
| Example 52 | | PSiO—Pd/TiO$_2$ | 97 | ○ |
| Example 53 | | PNCO-Pd/MgO | 95 | ○ |
| Example 54 | | PEI-Pd/ZrO$_2$ | 92 | Δ |
| Example 55 | | PSiOH—Pd/Al$_2$O$_3$ | 82 | ⊙ |
| Comparative Example 4 | | Pd/C | 75 | X |
| Example 56 | Sonogashira | PSiOH—Pd/Al$_2$O$_3$ | 85 | ⊙ |
| Example 57 | | PSiO—Pd/TiO$_2$ | 80 | ○ |
| Example 58 | | PNCO-Pd/MgO | 82 | ○ |
| Example 59 | | PEI-Pd/ZrO$_2$ | 83 | ○ |
| Comparative Example 5 | | Pd/C | 79 | X |
| Example 60 | Suzuki-Miyaura | PSiOH—Pd/Al$_2$O$_3$ | 82 | ⊙ |
| Example 61 | | PSiO—Pd/TiO$_2$ | 79 | ○ |
| Example 62 | | PNCO-Pd/MgO | 80 | Δ |
| Example 63 | | PEI-Pd/ZrO$_2$ | 76 | Δ |
| Comparative Example 6 | | Pd/C | 78 | Δ |

* Pd Leakage
Not Found at All –> ⊙
Found Very Trace Amount –> ○
Found Trace Amount –> Δ
Found Substantial Amount –> X

[Oxidation Reaction Using Polymer-Supported Pd Catalyst]

A DMA solution containing 1.0 mmol of 1-decene is prepared, and 0.05 mmol of a Pd catalyst, (0.15 mm of) copper (II) chloride dihydrate, and a small amount of H$_2$O are added thereto to make a suspension and to be stirred in an oxygen gas atmosphere at 1 atmospheric pressure for several hours. The catalyst is then removed from the suspension by filtration. Subsequently, the filtrate is concentrated for purification by column chromatography to obtain 2-decanone as an oxidation product.

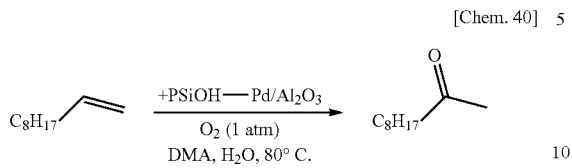

[Chem. 40]

[Hydrosilylation Reaction Using Polymer-Supported Platinum Catalyst]

A hexane solution containing 1.0 mmol of diphenylacetylene and 1.5 mmol of triethoxysilane is prepared, and 0.05 mmol of a platinum catalyst is added to be stirred at 60° C. for several hours. The platinum catalyst is then removed from the suspension by filtration. Subsequently, the filtrate is concentrated for purification by column chromatography to obtain a hydrosilylation product.

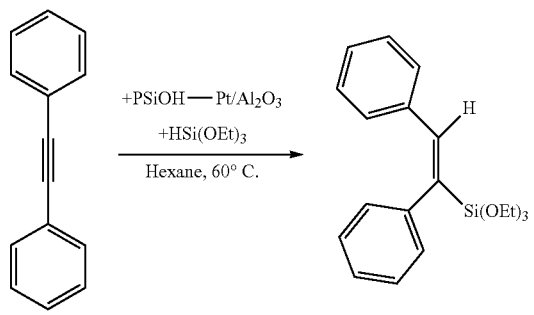

[Chem. 41]

The invention claimed is:

1. A method of producing a catalyst, the method comprising:
    preparing a first compound including a metal atom, and a polysiloxane polymer; and
    performing a reaction between the first compound and the polysiloxane polymer, wherein:
    the catalyst is formed through at least the reaction;
    the metal atom is at least one metal selected from the group consisting of palladium, platinum, ruthenium, rhodium, silver, gold, copper, nickel, cobalt, iron, chromium, manganese, technetium, osmium, molybdenum, tungsten, iridium, rhenium, titanium, zirconium, hafnium, tantalum, niobium, and vanadium; and
    the polysiloxane polymer has an oxyhydrosilylene structural unit.

2. The method of claim 1,
    wherein in the reaction between the first compound and the polysiloxane polymer, insertion of the metal atom of the first compound into a bond between a silicon atom and a hydrogen atom of the oxyhydrosilylene structural unit occurs.

3. The method of claim 1, wherein the catalyst includes an inorganic member or an organic member.

4. The method of claim 3, further comprising
    preparing the inorganic member or the organic member.

5. The method of claim 4, wherein
    the reaction between the first compound and the polysiloxane polymer is carried out in the presence of the inorganic member or the organic member.

6. The method of claim 4, wherein the inorganic member or the organic member is added after the reaction between the first compound and the polysiloxane polymer.

7. The method of claim 1, wherein the polysiloxane polymer is at least one selected from the group consisting of poly(oxymethylhydrosilylene), poly(oxydimethylsilylene)(oxymethylhydrosilylene) and poly(oxydimethylsilylene)(oxydihydrosilylene).

* * * * *